(12) United States Patent
Pettersson et al.

(10) Patent No.: US 8,805,658 B2
(45) Date of Patent: Aug. 12, 2014

(54) REPOSITIONING OF COMPONENTS RELATED TO CRANIAL SURGICAL PROCEDURES IN A PATIENT

(75) Inventors: Andreas Pettersson, Gothenburg (SE); Izidor Brajnovic, Rydal (SE); Henrik Petersson, Gothenburg (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 215 days.

(21) Appl. No.: 12/933,140

(22) PCT Filed: Mar. 17, 2009

(86) PCT No.: PCT/EP2009/001931
§ 371 (c)(1),
(2), (4) Date: Nov. 23, 2010

(87) PCT Pub. No.: WO2009/115283
PCT Pub. Date: Sep. 24, 2009

(65) Prior Publication Data
US 2011/0060558 A1    Mar. 10, 2011

(30) Foreign Application Priority Data
Mar. 19, 2008  (EP) ..................................... 08005146

(51) Int. Cl.
*G06G 7/48*    (2006.01)

(52) U.S. Cl.
USPC .......................................................... 703/6

(58) Field of Classification Search
USPC ....................................... 703/1, 6; 433/201.1
See application file for complete search history.

(56) References Cited

U.S. PATENT DOCUMENTS

| 4,663,720 A | 5/1987 | Duret et al. |
| 5,320,529 A | 6/1994 | Pompa |
| 5,448,472 A | 9/1995 | Mushabac |
| 5,725,376 A | 3/1998 | Poirier |

(Continued)

FOREIGN PATENT DOCUMENTS

| EP | 1500380 | 1/2005 |
| WO | WO 2006/014131 | 2/2006 |
| WO | WO 2007/009719 | 1/2007 |

OTHER PUBLICATIONS

Ganz, "Presurgical Planning With CT-Derived Fabrication of Surgical Guides", American Association of Oral and Maxilafacial Surgeons, 2005, pp. 59-71.*

(Continued)

*Primary Examiner* — Omar Fernandez Rivas
*Assistant Examiner* — Herng-Der Day
(74) *Attorney, Agent, or Firm* — Knobbe, Martens, Olson & Bear, LLP

(57) ABSTRACT

Methods, systems, and computer-readable media are disclosed herein for virtually planning a cranial guided surgery in a subject. These include, in some embodiments, generating a first data set based on input data obtained of a physical reference structure having a defined fixed relation to a bone structure of said subject and generating a second data set based on input data obtained of a master structure for a surgical template, where the master structure has a defined relation to said physical reference structure. Further, in some embodiments, a third data set for production of said surgical template can be generated based on the first data set and the second data set, wherein the relation of said physical reference structure to said master structure is preserved.

18 Claims, 12 Drawing Sheets

(56) References Cited

U.S. PATENT DOCUMENTS

| | | | |
|---|---|---|---|
| 5,752,376 A | 5/1998 | Vittorio et al. | |
| 5,768,134 A | 6/1998 | Swaelens et al. | |
| 5,857,853 A | 1/1999 | Van Nifterick | |
| 5,967,777 A * | 10/1999 | Klein et al. | 433/75 |
| 6,319,000 B1 | 11/2001 | Branemark | |
| 6,319,006 B1 | 11/2001 | Scherer et al. | |
| 6,672,870 B2 | 1/2004 | Knapp | |
| 6,788,986 B1 | 9/2004 | Traber et al. | |
| 6,793,491 B2 * | 9/2004 | Klein et al. | 433/173 |
| 7,322,824 B2 * | 1/2008 | Schmitt | 433/215 |
| 7,331,786 B2 | 2/2008 | Poirier | |
| 7,572,125 B2 | 8/2009 | Brajnovic | |
| 7,835,811 B2 * | 11/2010 | Schmitt | 700/98 |
| 7,845,943 B2 * | 12/2010 | Meitner | 433/75 |
| 7,942,668 B2 | 5/2011 | Brajnovic et al. | |
| 7,950,924 B2 | 5/2011 | Brajnovic | |
| 8,142,192 B2 * | 3/2012 | Malo | 433/173 |
| 8,157,565 B2 | 4/2012 | Jones et al. | |
| 8,170,327 B2 * | 5/2012 | Glor et al. | 382/154 |
| 8,186,999 B2 | 5/2012 | Andersson et al. | |
| 2004/0259051 A1 | 12/2004 | Brajnovic | |
| 2005/0170311 A1 | 8/2005 | Tardieu et al. | |
| 2009/0187393 A1 * | 7/2009 | Van Lierde et al. | 703/11 |
| 2009/0325122 A1 | 12/2009 | Brajnovic et al. | |
| 2010/0332248 A1 | 12/2010 | Pettersson | |
| 2011/0008751 A1 | 1/2011 | Pettersson | |
| 2011/0010187 A1 * | 1/2011 | Andersson et al. | 705/2 |
| 2012/0123576 A1 | 5/2012 | Pettersson et al. | |

OTHER PUBLICATIONS

Balshi et al., "Surgical Planning and Prosthesis Construction Using Computed Tomography, CAD/CAM Technology, and the Internet for Immediate Loading of Dental Implants", Journal Compilation, 2006, pp. 312-322.*

International Search Report of PCT/EP2009/001931 mailed Jun. 25, 2009.

* cited by examiner

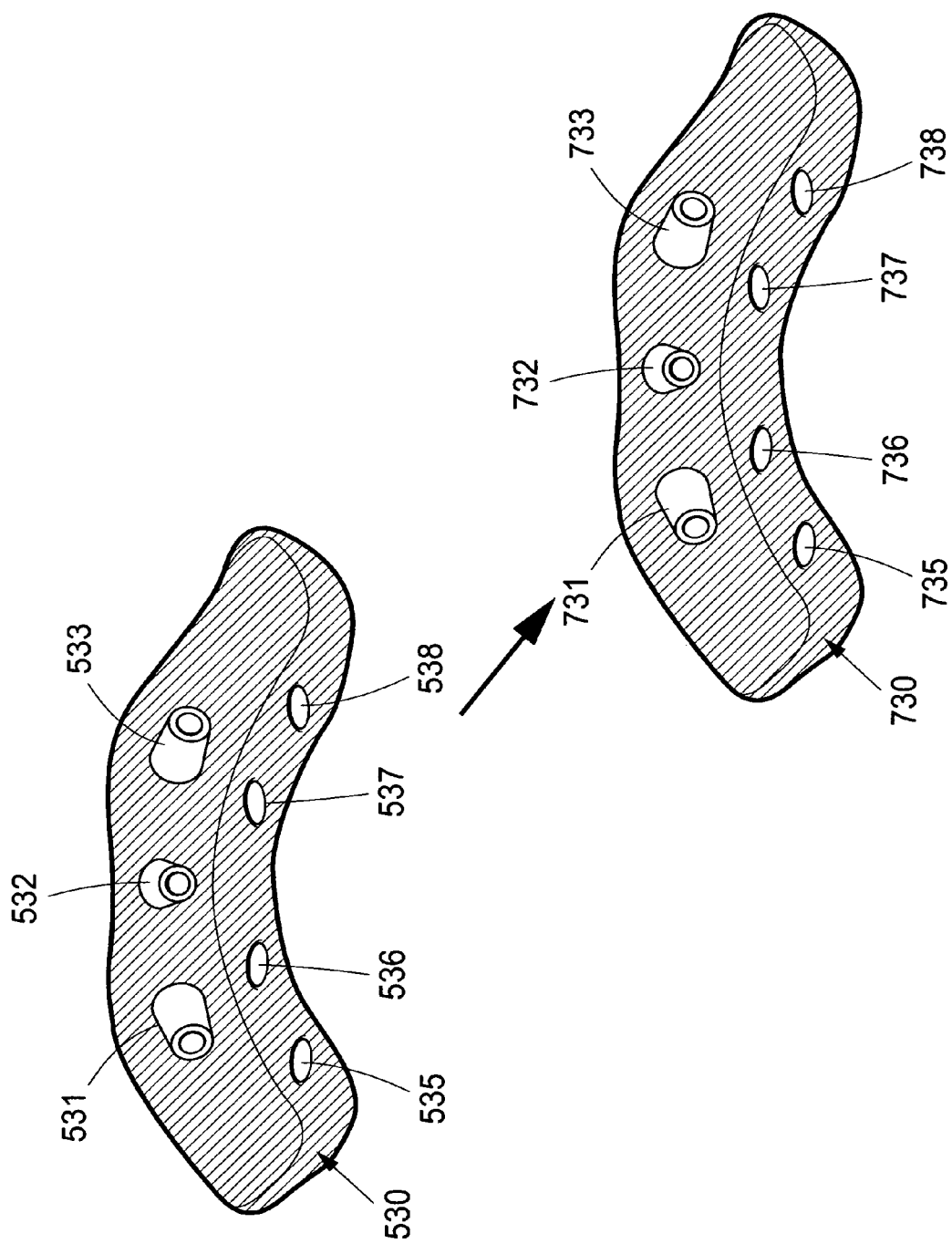

REPOSITIONING OF COMPONENTS RELATED TO CRANIAL SURGICAL PROCEDURES IN A PATIENT

CROSS-REFERENCE TO RELATED APPLICATIONS

This application is a national stage application under 35 U.S.C. §371 of PCT Application No. PCT/EP2009/001931 designating the United States, filed on Mar. 17, 2009 and claiming priority to European Patent Application No. 08005146, filed on Mar. 19, 2008. The PCT Application was published in English as WO 2009/115283 A1 on Sep. 24, 2009, and claims the benefit of the earlier filing date of European Patent Application No. 08005146.9, filed on Mar. 19, 2008. The contents of PCT Application No. PCT/EP2009/001931, including publication WO 2009/115283 A1, and European Patent Application No. 08005146.9, are incorporated herein by reference in their entirety for all purposes.

FIELD OF THE INVENTION

This invention pertains in general to the field of cranial surgery, including dentistry. More particularly the invention relates to a method and system for repositioning of components in relation to a patient during cranial surgical procedures, including virtual planning of said cranial surgical procedure and providing production data for the components based on said virtual planning. The invention also pertains to components, manufacturing processes for said components, and computer programs facilitating the repositioning.

BACKGROUND OF THE INVENTION

Bone resorption in edentulous subjects provides a challenge in many aspects of dental restorative procedures. For instance during drill and implant guided surgery a surgical template is placed directly on the mucosa. However, in edentulous subjects a defined, stable position of the surgical template may be not given, e.g. due to bone resorption of the alveolar ridge. Furthermore, there may be no unambiguous anatomical structure in the oral cavity giving a clear-cut positioning of the surgical template in the subject. The same issue may occur at other cranial sites, e.g. when planning facial reconstructions, such as including ear, nose, or eye prosthesis.

Hence, when a surgical template is fixed to a subject, the position of the surgical template may differ largely from a desired position, e.g. pre-determined in a virtual planning based on input data related to a position of a structure having a defined position to the subject's anatomy during data acquisition, such as a radiographic guide. Positioning of the real surgical template manufactured based on data of the virtual planning is thus difficult. This may inherently lead to a non-desired positioning of implants in the subject, and thus non-desired results of surgical restorative procedures, such as dental restorative procedures.

In US2007077535 a method is disclosed dealing with this issue. The disclosed method is a model-based dental restorative method relying on the use of positioning screws having fixed positions. The disclosed method is a purely mechanical method where the positioning screws serve as temporary posts intended to provide reliable positioning of e.g. drilling templates. A conventional, plaster cast based production of drilling templates is disclosed, wherein the positioning screws are screwed into the lingual-oral or palatal area (i.e. the oral area of the lower or upper jaw oriented towards the tongue) and/or into the alveolar process (the thickened ridge of bone that contains tooth sockets) so that an impression of the position of the positioning screws and capturing the actual structure of the patient's jaw is taken. Subsequently, corresponding positioning screws are installed in the impression; and finally any further technical dental work is carried out on the impression, namely the manufacture of a drilling template for the implants to be installed. The drilling template thus manually created is positioned in the oral cavity of the patient by snapping it onto the positioning screws that thus serve as re-positioning aides.

However, the method disclosed in US2007077535 is purely model based, and has a number of drawbacks.

For instance, a surgical template is produced in a conventional model-based manner, whereby sources of errors as conventionally known are not eliminated, e.g. shrinkage of each of an impression material and subsequently of a casting material for a surgical template cast form and finally the material of the surgical template in the cast are contributors to an error chain, whereby accuracy is lost in each process step. This lack of accuracy may not be acceptable in some medical procedures.

Therefore, the method disclosed in US2007077535 may not work satisfactory, in particular for critical applications, such as implantation of zygoma implants.

Further, a mass customization of surgical templates to be used in dental restorative procedures is not feasible according to the method disclosed in US2007077535. Each single surgical template needs an enormous amount of manual adaptation on physical casts and models.

Hence, an improved method and system for facilitating or providing precise repositioning of components related to cranial surgical procedures, such as dental procedures in at least partly edentulous subjects, e.g. suffering from bone resorption, would be advantageous.

SUMMARY

Accordingly, embodiments of the present invention preferably seek to mitigate, alleviate or eliminate one or more deficiencies, disadvantages or issues in the art, such as the above-identified, singly or in any combination by providing a method, a system, and a computer program according to the appended patent claims.

According to a first aspect of the invention, a method is provided. The method is a computer-implemented method of virtually planning a cranial drilled implant guided surgery in a subject. The method comprises generating a first data set based on input data obtained from a reference structure having a defined fixed relation to a bone structure of said subject, generating a second data set based on input data obtained from a master structure for a surgical template, said master structure having a defined relation to said reference structure, and associating said first data set with said second data set such that said relation of said reference structure to said master structure is preserved whereby a third data set for production of said surgical template is provided.

According to a second aspect of the invention, a method of producing a real surgical template comprising the method of the first aspect of the invention for virtually planning a cranial drilled implant guided surgery, comprising providing a data set for production of real said surgical template based on said virtual planning, and producing a real surgical template from said data set for production, such that said real surgical template is devised for use in a real cranial drilled implant guided surgery corresponding to said virtually planned cranial drilled implant guided surgery.

According to a third aspect of the invention, a system is provided. The system is devised for computer-implemented virtually planning a cranial drilled implant guided surgery of a patient, wherein the system is devised for implementing the method according to the first aspect of the invention. The system comprises a unit for virtual planning of a cranial drilled implant guided surgery of a patient; and a unit for generating data based on said virtual planning; wherein said unit for generating data based on said virtual planning comprises a unit for generating a first data set based on input data obtained from a reference structure having a defined fixed relation to a bone structure of said subject; a unit for generating a second data set based on input data obtained from a master structure for a surgical template, said master structure having a defined relation to said reference structure, and a unit for associating said first data set with said second data set such that said relation of said reference structure to said master structure is preserved whereby a third data set for production of said surgical template is provided; wherein said third data set is configured for subsequent use in production of a real surgical template procedure for said cranial drilled implant guided surgery, and/or for controlling a device configured to facilitate said cranial drilled implant guided surgery.

According to a fourth aspect of the invention, a computer program for processing by a computer is provided. The computer program is a computer program for virtually planning a cranial drilled implant guided surgery of a patient, for processing by a computer comprising a first code segment for generating a first data set based on input data obtained from a reference structure having a defined fixed relation to a bone structure of said subject; a second code segment for generating a second data set based on input data obtained from a master structure for a surgical template, said master structure having a defined relation to said reference structure, and a third code segment for associating said first data set with said second data set such that said relation of said reference structure to said master structure is preserved whereby a third data set for production of said surgical template is provided; wherein said third data set is configured for subsequent use in production of a real surgical template procedure for said cranial drilled implant guided surgery, and/or for controlling a device configured to facilitate said cranial drilled implant guided surgery.

The computer program may be implemented on a computer-readable medium. The computer program of the fourth aspect of the invention may be devised for enabling carrying out of the method according to the first aspect of the invention.

Further embodiments of the invention are defined in the dependent claims, wherein features for the second and subsequent aspects of the invention are as for the first aspect mutatis mutandis.

Some embodiments of the invention provide for repositioning of a surgical template to the same position as a radiographic guide was positioned during data acquisition with high precision.

Some embodiments of the invention also provide for virtual surgical planning that is precise and not at random.

Some embodiments provide for a fixed retention of a surgical template, efficiently preventing a loosening, migration or move thereof. This may in particular be advantageous for critical applications, such as implantation of zygoma implants.

Some embodiments provide for precise and secure re-positioning of surgical templates in fully edentulous patients.

Some embodiments provide for precise and secure re-positioning of surgical templates in substantially edentulous patients.

Some embodiments provide for precise and secure re-positioning of surgical templates in patients lacking fixed anatomical reference points.

Some embodiments provide for threaded reference bore channels into which structures are insertable that provide a secure re-positioning of surgical templates.

Some embodiments provide for anatomically correct positioned dental restorations by providing a virtual planning based on anatomically fixed reference points in combination with the use of artificial fixed or removable reference elements.

It should be emphasized that the term "comprises/comprising" when used in this specification is taken to specify the presence of stated features, integers, steps or components but does not preclude the presence or addition of one or more other features, integers, steps, components or groups thereof.

These and other aspects, features and advantages of which embodiments of the invention are capable of will be apparent and elucidated from the following description of embodiments of the present invention, reference being made to the accompanying drawings, in which FIG. 1 is a flow chart showing an embodiment of a method of the invention;

FIG. 7 is a schematic illustration of design and production of said surgical template from data provided from said virtual planning;

Figure 1:
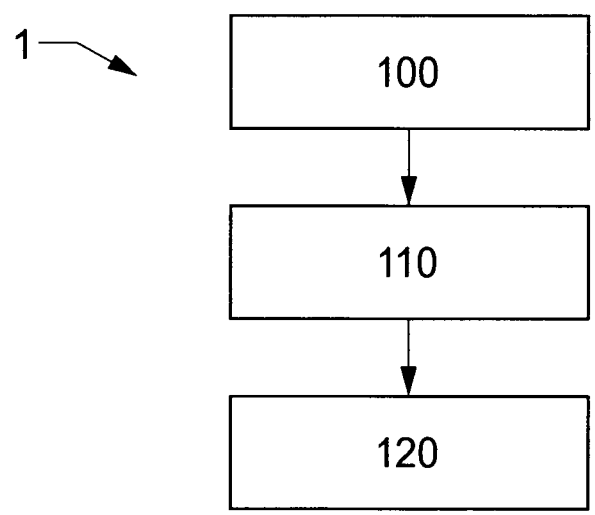

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to a dental implant. However, it will be appreciated that the invention is not limited to this application but may be applied to many other cranial drilled implant guided surgeries in a subject including for example of maxillofacial implants, or implant anchored cranial or facial prosthesis, such as ear nose, or eye prosthesis.

Below embodiments of a method of virtually planning a cranial drilled implant guided surgery in a subject is described in more detail, comprising virtually planning of drill and implant guided surgery, self drilling implants, etc.

The method 1, illustrated in FIG. 1, comprises generating 100 a first data set based on first input data obtained from a reference structure having a defined fixed relation to a bone structure of the subject.

The first input data, on which the first data set is based, may be obtained in various ways and from various data generating sources, for instance CT scanning, MR scanning, Ultrasonic imaging, Optical Imaging, Surface scanning, Touch probe scanning, 3D photography, Intraoral scanners, etc.

The reference structure may be devised to be provided for obtaining input data by data acquisition using e.g. the above mentioned data generating sources. In some embodiments, the reference structure may be a manufactured structure devised for providing a defined fixed relation to a cranial bone structure of a patient and configured to provide a (first) set of input data. The reference structure may be an anchoring element devised for anchoring in bone tissue of the cranial bone structure and devised for facilitating anchoring of a surgical template in a fixed relation to the bone tissue. The reference structure may for instance be a temporary anchoring implant, an anchoring pin, pre-existing implants, etc.

The reference structure may in some embodiments be temporary fixed in bone tissue.

For instance a temporary anchoring implant may be inserted into patient bone tissue, where it is left during registering of data thereof. It may as well be left in that position during a subsequent period of time that for instance is used for virtual planning of a surgical procedure, and for production of a real surgical template. First during the real surgical procedure, the temporary anchoring implant may be removed from the bone tissue, leaving a threaded reference bore channel for insertion of an anchoring screw that is guided by a guide sleeve of the surgical template and thus locks the surgical template in a precise manner into position.

Another example for a temporary fixed reference structure is an anchoring screw that is devised to lock a master structure, such as a radiographic guide, in a cranial place during registering of data. Then the anchoring screw may be removed and the master structure, such as the radiographic guide, may be removed, leaving a threaded bore in a cranial bone structure. The threaded bore left by the anchoring screw may then be filled with a temporary anchoring implant inserted therein and left in place until the real surgical procedure, as explained in the previous paragraph. The anchoring screw or the temporary anchoring implant may thus in some embodiments advantageously be devised to avoid osseointegration thereof with surrounding bone tissue, such that a subsequent removal of the structure is facilitated.

The reference structure may in some embodiments be permanently fixed in bone tissue, such as is the case for an existing anchoring implant, such as a dental implant, that was previously implanted in the patient's bone tissue.

In addition, a plurality of identical, similar or arbitrarily different reference structures may be present in the patient and used for providing input data for the first data set.

The reference structure may have a pre-defined density and/or shape for identifying a position, direction and/or orientation thereof.

Figure 4:
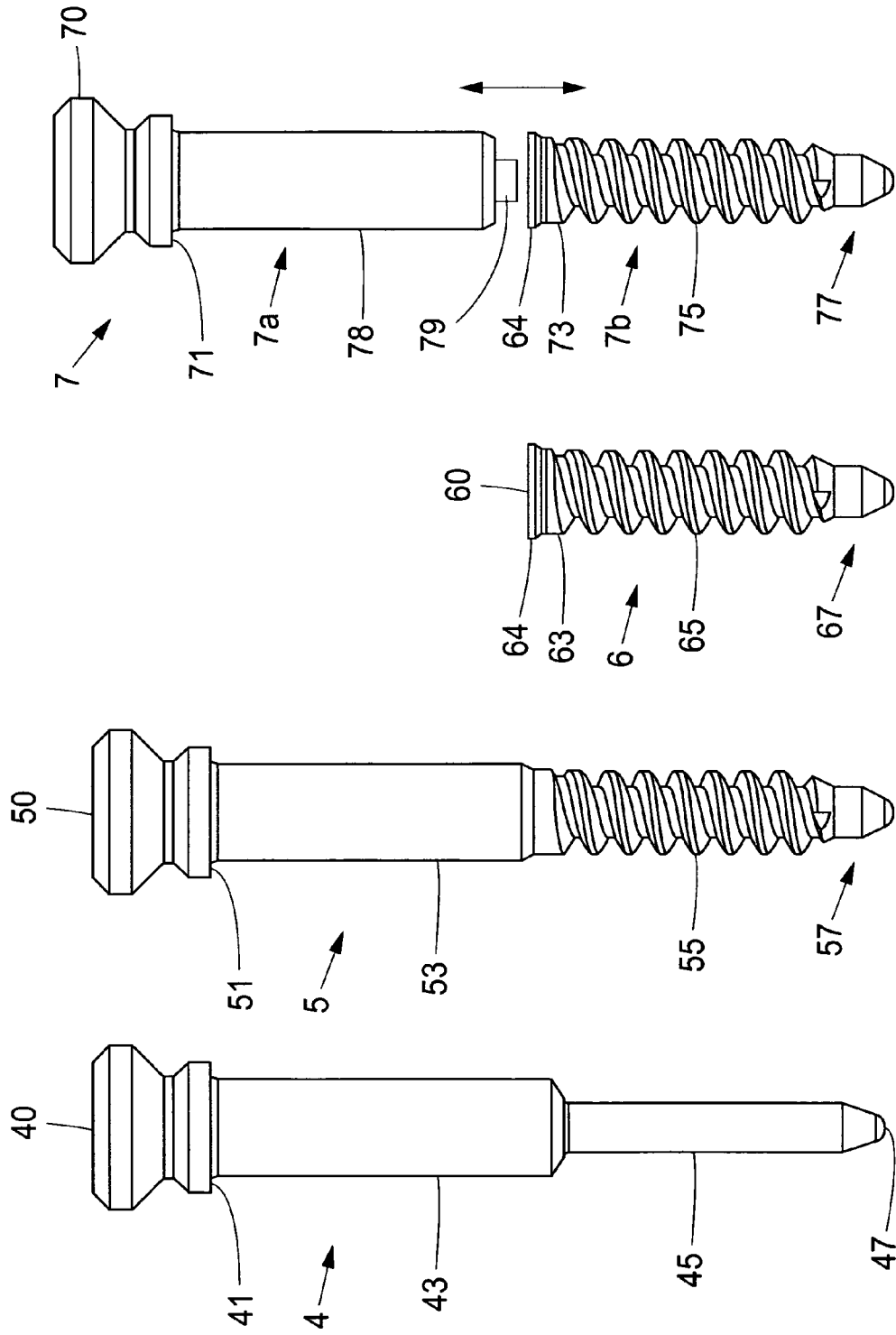
FIGS. 4A, 4B, 4C, 4D are lateral views of an anchor pin, an anchor screw and a temporary anchoring implant, and a two-part anchor screw respectively.

In some embodiments, such as illustrated in FIGS. 4A, 4B and 4C, the reference structure may be an anchoring screw 5, 7 devised for anchoring a surgical template in a fixed relation to bone tissue, wherein said anchoring screw 5, 7 may comprise an apical end 57, 77, a threaded anchoring section 55, 75 for temporary anchoring in bone tissue, a sleeve section 53, 73 for sliding insertion into a guide sleeve of a surgical template, a stop shoulder 51, 71 matingly cooperating with a top shoulder of said guide sleeve, and a head section 50, 70.

The reference structure may be a two-part anchoring screw 7 (FIG. 4D) comprising a proximal part 7a comprising said head section 70, stop shoulder 71, and sleeve section 73; and a distal part 7b comprising said threaded anchoring section 75, and apical end 77; and a connection interface for releasably locking the proximal part 7a and the distal part 7b to each other. The proximal part 7a may comprise a connection interface adapted to releasably engage with a corresponding connection interface of a dental implant.

The reference structure may be anchoring element in form of a temporary anchoring implant 6 (FIG. 4C) comprising an apical end 67, a threaded anchoring section 65 for temporary anchoring in bone tissue; a transition section 63 arranged in a fixed relation to a longitudinal axis of the temporary anchoring implant 6; and a head section 60 having a top part 64 with a slightly extended diameter compared to an outer diameter of the threaded section 65; wherein said top part 64 of said head section 60 is devised for apposition to soft tissue.

The apical end of the reference structure may comprise a tip that has a conical, frusto-conical, or reduced diameter shape in relation to the maximum outer diameter of the threaded section 55, 65, 75, wherein said tip proximally adjoins a cylindrical section adjoining the distal end of threaded section 55, 65, 75, and wherein said cylindrical section has approximately a diameter corresponding to a diameter of a bore into which the threaded section 55, 65, 75 is configured to be inserted. This provides for a precise and controlled insertion of the reference structure into bores in bone tissue.

The method further comprises generating 110 a second data set based on second input data obtained from a master structure for a surgical template.

The second input data, on which the second data set is based, may be obtained in various ways and from various data generating sources, for instance CT scanning, MR scanning, Ultrasonic imaging, Optical Imaging, Surface scanning, Touch probe scanning, 3D photography, Intraoral scanners, etc.

The master structure may for instance be a radiographic guide, a dental impression, a portion of the subject's actual anatomical situation, such as a bone tissue surface and/or topography or a soft tissue surface and/or topography, etc.

The second data set may comprise topographical data for a cranial anatomical structure towards which the real surgical template is to be arranged, fit, or otherwise fixated during a real surgical procedure, and is based on the second input data.

The second input data may, thus, provide a basis for providing data for a portion of a surgical template that will be arranged towards and/or abutting the cranial anatomical structure, for instance during a surgical procedure.

The second data set may comprise data for the topographical form of an oral soft tissue surface structure, e.g. based on input data from a radiographic guide (i.e. the portion of the radiographic guide abutting against the soft tissue provides data as a basis for the second data set). The second data set thus provides a basis for providing data for a portion of a surgical template that will be arranged towards and/or abutting the soft tissue and has a corresponding form.

The second data set may comprise data for the topographical form of a bone.

The second data set may be a 3D surface model of the master structure.

The master structure has a defined relation to the reference structure at least at the time of data acquisition. Said defined relation is a defined fixed relation at least during said occasion when said second data set is generated. For instance, in case the master structure is a radiographic guide, this may be removed after data acquisition from the patient. For instance in case the master structure is a fixed anatomical structure of the patient it remains in position after data acquisition of the second input data set.

The method further comprises associating 120 the first data set with the second data set such that the relation of the reference structure to the master structure is preserved whereby a third data set for production of the surgical template is provided.

The third data set may thus comprise information elements for the first data set based on the first input data obtained from the reference structure having a defined fixed relation to the bone structure of the subject, as well as the second data set based on the second input data obtained from the master structure for the surgical template. As the master structure has a defined relation to the reference structure, at least fixed at the time of data acquisition, the real surgical template produced from the third data set may be precisely re-positioned in relation to the reference structure and thus in relation to the bone structure in the same manner as the master structure at the time of data acquisition of the second input data set.

The surgical template may be a surgical template for drill and implant guided surgery, or other medical products devised for use in cranial surgical procedures, as described further below.

In this context the term "associating" may comprise putting or matching the first and the second data set in a common coordinate system; or linking the first data set and the second data set in a fixed relation to each other; or placing the first data set and the second data set in a mutual relationship; or bringing the first data set and the second data set into conjunction, proper coordination or relation; or connecting the first data set and the second data set with each other.

The purpose of the method is to facilitate positioning of a real surgical template during a real cranial surgical procedure at a desired position and in a desired relation to an anatomical structure of a patient. This positioning is provided with high precision and accuracy in order to correspond as exactly as possible to a virtual planning of the cranial surgical procedure. The positioning comprises re-positioning for instance when the surgical template is to be positioned at the same position as another component, such as a radiographic guide, has been positioned previously during data acquisition for providing input data to said virtual planning of the cranial surgical procedure. Hence, the method facilitates re-positioning a surgical template at the same position in relation to the cranium as a radiographic guide has been positioned previously.

In addition, a reliable fixation of a surgical template is provided during a cranial surgical procedure. Moreover, the fixation of the surgical template is simple and reliably releasable upon the surgical procedure being finished.

Cranial surgery in the context of the present application includes drill- and implant guided surgery performed on body regions from the neck upwards, i.e. dental surgery, maxillofacial surgery, or surgery in order to position implant fixated prosthesis for other cranial body parts, such as a nose, ear, or eye. The cranial surgery may also comprise other operations, such as bone replacement, bone reduction, or build up of bone structures.

The reference structure having a defined position, and direction and/or orientation is registered and data thereof is provided for virtual planning of a drill and implant guided surgical procedure. The virtual planning comprises directly or indirectly defining a position for a re-positioning component, such as anchoring sleeves 731, 732, 733 (see FIG. 9A), in relation to a master structure. The master structure in combination with the re-positioning component may form the surgical template.

When the virtual planning is finalized, data (third data set) useful for producing a real surgical template is provided. High precision of the real surgical procedure, as previously virtually planned, is achieved because the real surgical template used during the real surgical procedure thus is positioned with high precision to a desired position in the subject. Consequently, also drills and implants are guided and positioned in the bone tissue of the patient with high precision by means of the real surgical template. The implants may for instance be dental implants or anchoring implants for other cranial or facial prosthesis.

The virtual planning of the dental implants may be made according to the method of the same applicant as the present application, as described in unpublished patent application SE0701296-6 of the same applicant as the present application, which is incorporated herein by reference for all purposes. According to this method positions of at least one tooth of dental restorations and thus suitable positions of dental implants are determined based on anatomically fixed reference points that are anatomically stable. Thus dental restorations are provided that have teeth which are patient-specifically anatomically correct positioned.

Examples of the data registering, data association, virtual planning of the surgical procedure, production of the surgical template, and the real surgical procedure are given further below.

In some exemplary embodiments a) to c) the first data set and the second data set are given as follows:

A) First Data Set:
- a reference structure is an artificial reference structure positioned in bone tissue at a site of the planned surgical procedure, e.g. a temporary anchoring implant or an existing dental implant in the oral cavity of the patient, and is used for generating a first input data set;
- a master structure is a radiographic guide, i.e. a copy of an anatomical restoration desired to be positioned at the site of the planned surgical procedure, such as a dental restoration including a teeth prosthesis, a nose prosthesis, an ear prosthesis, etc.

A first data set is generated based on first input data obtained from the artificial reference structure having a defined fixed relation to a bone structure of the patient.

The first input data may be obtained by CT scanning the site of the planned surgical procedure together with the radiographic guide positioned at the site of the planned surgical procedure; the radiographic guide does not need to be fixated to the bone structure at the site of planned surgical procedure, but it needs to have a defined spatial relation thereto when generating the first input data set, such as a dental prosthesis inserted into the mouth of the patient and kept in position; wherein the defined spatial position may be registered by means of suitable fiducial markers, such as gutta percha markers on an acrylic radiographic guide (thus avoiding imaging artefacts). The first input data set thus comprises data for the reference structure and the position of the radiographic guide in relation thereto (determinable thanks to the fiducial markers).

The first input data set may comprise X/Y/Z coordinates for the reference structure, e.g. the apical and coronal coordinates of the reference structure.

From this first input data the position of the reference structure is provided.

The first data set thus may be derived based on the first input data set. For instance, the position of the reference structure is provided by the first input data set.

From this position (and knowledge of the structure of the reference structure), for instance coordinates of an anchoring sleeve may have a defined relation to the reference structure. Thus the first data set may comprise data for the position of an anchoring sleeve in relation to the reference structure. The first data set may thus define the position of the anchoring sleeve in production data for a real surgical template. The first data set may be coordinates already calculated for the anchoring sleeve.

The first data set may also be indirectly related to the reference structure. One example is voxel based matching, e.g. matching a defined form and/or HU (Hounsfield Unit) value of a reference structure for identifying the position in space of the reference structure.

second data set: High resolution data for the master structure is obtained, e.g. by a second CT scan, providing a second input data set; In case of an acrylic radiographic guide having gutta percha fiducial markers attached thereto, the second input data set comprises data for the positions of the gutta percha markers and the structure of the radiographic guide itself. From this second input data set the second data set is generated, e.g. providing data for defining the portions of a surgical template to be arranged in oral cavity towards the soft tissue in the same position as during the occasion of data acquisition for the first input data (when the radiographic guide had a defined relation to the reference structure).

By associating the first data set and the second data set, the third data set is provided. From the third data set a real surgical template may be produced having portions for precise re-positioning towards or against soft tissue (based on the second data set) and having at least one unit for positioning the surgical template in relation to the reference structure (from the first data set—guide sleeve). Thus the surgical template produced from the third data may securely be locked into the desired position during the surgical procedure.

B) First Data Set:
    a reference structure is an artificial reference structure as in example a), and is used for generating a first input data set.
    a master structure is a radiographic guide comprising a radiopaque structure or material.

As in example a), the first input data set is obtained by CT scanning the site of the planned surgical procedure together with the radiographic guide positioned at the site of the planned surgical procedure. As the radiographic guide is radiopaque, both the structure and position thereof is determinable from the first input data set.

The second input data set is a sub-set of the first input data set, namely the structural information obtained from the CT scan of the radiopaque structure of the radiographic guide. A re-positioning is made more reliable by means of aligning a real surgical template produced based on the first and second data set, generated from the first and second input data set, and locked to the position of the reference structure during the real surgical procedure.

C) First Data Set:
    a reference structure is an artificial reference structure as in example a), and is used for generating a first input data set.
    a master structure is a surface of an existing anatomical structure of the patient at the site of the planned surgical procedure. The existing anatomical structure may be a surface of bone tissue, or a surface of soft tissue, which are substantially immovable in relation to the reference structure.

Examples for a surface of bone tissue comprise the outer surface of the mandible or of the maxilla which is e.g. available during a "flapped" dental surgery. A surgical template may be produced for resting on that bone surface during the real surgical procedure, fixed in position to the reference structure anchored to the bone tissue. Examples for a surface of soft tissue comprise the surface of the gingival, e.g. available during "flapless" surgery. A surgical template may be produced for resting on that gingival surface during the real surgical procedure, fixed in position to the reference structure anchored to the underlying bone tissue.

Second Data Set:
    the second input data set comprises data for the position and topography of the bone tissue surface and/or the soft tissue surface having a fixed relation to the reference structure. Thus the second data set is generated based on the second input data set. Having associated the first data set and the second data set, surfaces of the virtually planned surgical template may be planned to be brought in contact with the corresponding external surfaces of the bone tissue and/or soft tissue at the site of the planned surgical procedure. In addition, fixation facilitating elements, such as guide sleeves, are virtually planned based on the position and direction of the references structure. In combination, data is provided for producing a real surgical template—without the need of a radiographic guide for generating suitable input data for the virtual planning.

A specific embodiment of the virtual planning method is now described in more detail with reference to FIGS. 2 to 9.

Figure 2:
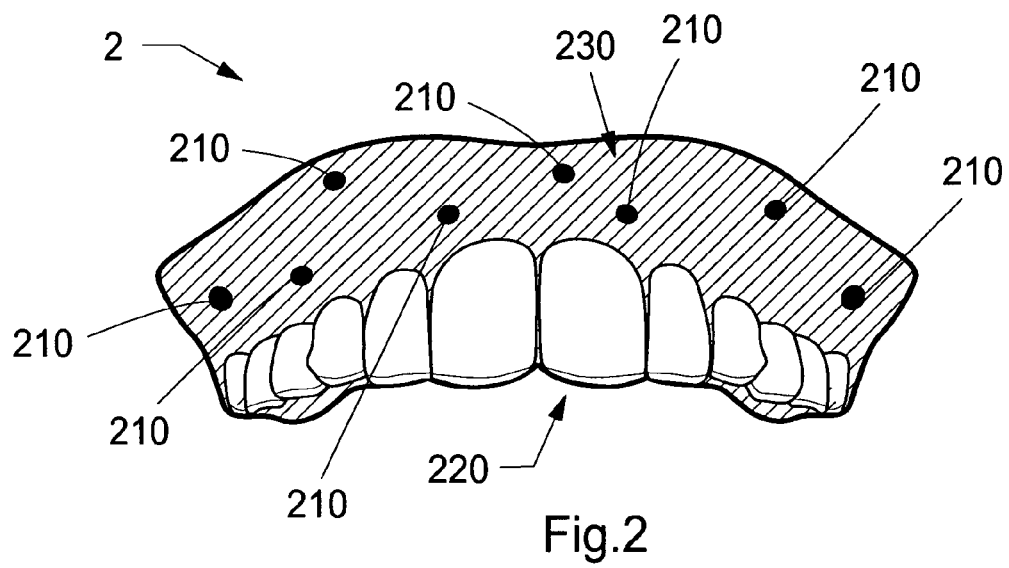
FIG. 2 is perspective view of a radiographic guide.

In FIG. 2 a master structure in form of a radiographic guide 2 is shown comprising a plurality of radiopaque fiducial markers 210, e.g. spherical markers produced of gutta percha for CT scanning.

The radiographic guide is used to simulate the teeth, the soft tissue surface and edentulous space during a CT scan. A radiographic guide is made of a non-radiopaque material, such as of acrylic or with similar density.

In fully edentulous cases, an existing or optimized prosthesis or a newly produced prosthesis of the patient may be used as a radiographic guide.

A radiographic guide may for instance be prepared in the following manner. An impression of both jaws and a bite registration index, such as an occlusal index, is made, wherein the bite index is made using a stiff material. For fully edentulous jaws, the bite registration may be made using the existing or optimized prosthesis or, if needed, a newly produced prosthesis, i.e. the corresponding to the radiographic guide. If the patient only has a few teeth in the opposing jaw and does not wear a partial prosthesis, the area where the teeth are missing is filled up with occlusion index material to make contact with the alveolar ridge. This is to ensure a well balanced bite registration.

Figure 3:
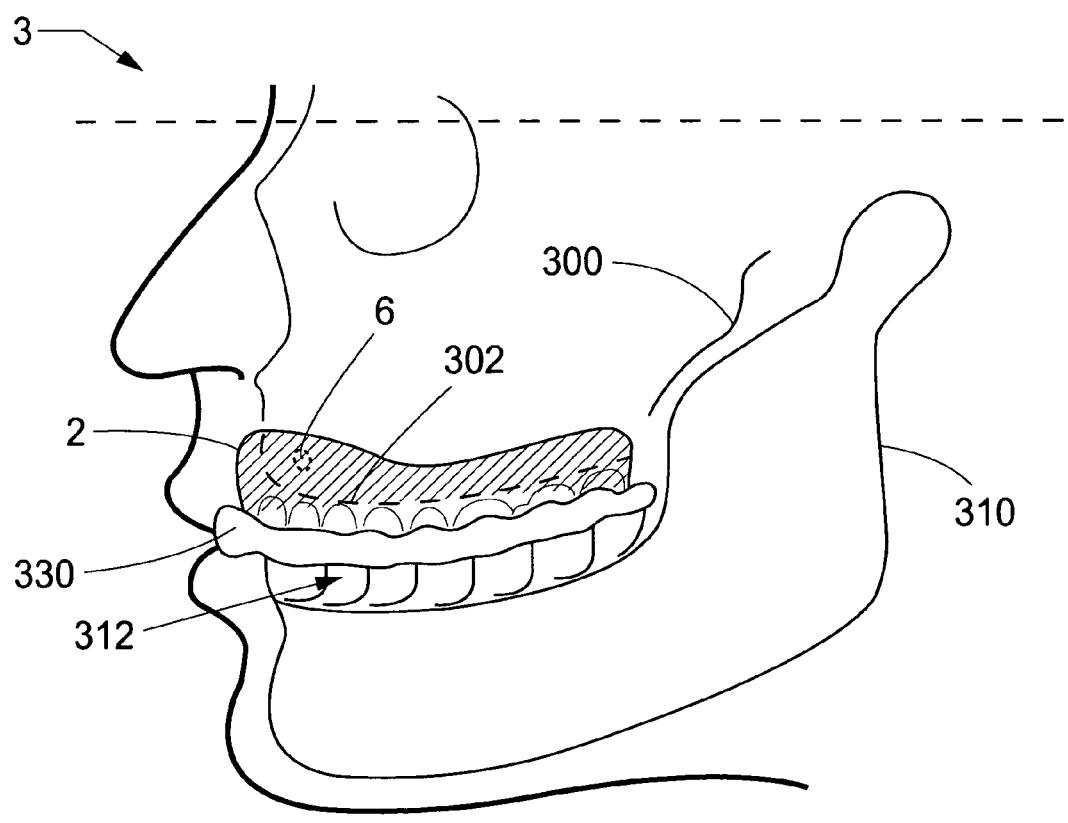
FIG. 3 is a schematic view of a cranial region of a subject with a radiographic guide, a bite index and a temporary implant.

A radiographic index 330 ensures the optimal bite of the patient and is used to make sure the radiographic guide is in an optimal position during the data generation, i.e. here a first CT scan. As illustrated in FIG. 2, the radiographic guide 2 is e.g. a replica of the patient's dental prosthesis having a first portion 230 corresponding to the soft tissue to be recreated by a dental restoration and for attachment to a jaw of the subject, for instance to the maxilla (upper jaw bone) 300 of the cranium 3 of the subject, as shown in FIG. 3. The radiographic guide furthermore comprises a second portion 220 corresponding to the teeth of the dental restoration.

An issue is that acrylic material used for producing radiographic guides from dental impressions is shrinking when it polymerizes. This fact contributes to the conventional difficulties of repositioning mentioned in the above section "background of the invention". This may be solved by using a triple tray for taking a dental impression and surface scanning the impression made, as described below.

A reference structure, in the present embodiment in form of a temporary anchoring implant 6, as shown in FIG. 4C, is inserted in the maxilla 300 of the subject. A surgeon may for instance position the temporary anchoring implant 6 so far into the jaw bone tissue that only a top part 64 of the head section 60 having a slightly extended diameter compared to the threaded section 65 protrudes into the soft tissue.

In this way, the radiographic guide 2 may easily slide over the protruding part of the temporary anchoring implant 6 with substantially no or only minor modification. This may be very advantageous as it in this case is ensured that a surgical template has sufficient material available for production.

In FIG. 3 a cranial region of the subject is shown with the radiographic guide 2, a bite index 330 and a temporary anchoring implant 6 in position for generation and/or registration of a first data set, comprising patient data and data for the reference structure as well as radiopaque portions of the radiographic guide, according to step 110 of the method. The mandible (lower jaw bone) 310 of the subject is in the example of the illustration of FIG. 3 shown with teeth 312 opposite the second portion 220 of the radiographic guide 2, separated by the bite index 330. The bite index 330 ensures a proper orientation of the radiographic guide in relation to the opposite jaw.

In FIG. 4A a conventional anchor pin 4 is shown having an apical end 47, an anchoring section 45 for anchoring in bone tissue, a sleeve section 43 for sliding insertion into a guide sleeve of a surgical template, a stop shoulder 41 matingly cooperating with a top shoulder of the guide sleeve, and a head section 40 for allowing handling of the anchor pin 4. Anchor pins 4 are conventionally used to fixate surgical templates to adjacent bone tissue. Guide sleeves for anchor pins are added to virtually planned surgical templates and real surgical templates are produced from data provided by means of this virtual planning.

In FIG. 4B an anchor screw 5 is shown having an apical end 57, a threaded anchoring section 55 for temporary anchoring in bone tissue, a sleeve section 53 for sliding insertion into a guide sleeve of a surgical template, a stop shoulder 51 matingly cooperating with a top shoulder of the guide sleeve, and a head section 50 for allowing handling of the anchor screw 5. The head section 50 may comprise a releasably lockable interface for an insertion tool, such as a socket wrench.

Anchor screws provide an improved locking of a surgical template to adjacent bone tissue, in comparison with the use of anchor pins 4.

In FIG. 4C a temporary anchoring implant 6 is shown having an apical end 67, a threaded anchoring section 65 for temporary anchoring in bone tissue, a transition section 63 arranged in a fixed relation to a longitudinal axis of the temporary anchoring implant 6, and a head section 60 for allowing handling of the temporary anchoring implant 6. The head section 60 may comprise a releasably lockable interface for an insertion tool, such as a socket wrench.

In FIG. 4D a two-part anchor screw 7 is shown. The anchor screw 7 comprises a first, distal part 7b and a second, proximal part 7a.

The distal part 7b comprises, like the temporary anchoring implant 6, an apical end 77, a threaded anchoring section 75 for temporary anchoring in bone tissue, a transition section 73 arranged in a fixed relation to a longitudinal axis of the distal part 7b.

The proximal part 7a comprises a sleeve section 78 for sliding insertion into a guide sleeve of a surgical template, a stop shoulder 71 matingly cooperating with a top shoulder of the guide sleeve, and a head section 70 for allowing handling of the temporary proximal part 7a. The head section 70 may comprise a releasably lockable interface for an insertion tool, such as a socket wrench.

The distal part 7b and the proximal part 7a comprise mating connection interfaces for providing a releasable connection of the two parts to each other. A distal end section of the proximal part 7a may for instance comprises a releasable protruding fixation element 79 for mating engagement with a corresponding recessed fixation element in the head section 64 of the distal part 7b. Fixation element 79 may be a thread for insertion into a corresponding threaded bore in the distal part 7b. In this manner the proximal part 7a and the distal part 7b may be assembled into a single unit arranged around a common longitudinal axis.

The assembled anchor screw 7 corresponds to the anchor screw 5 shown in FIG. 4B. However, the feature that the present anchor screw 7 may be divided into two parts has a number of advantages. For instance, the distal part 7b may be inserted into bone tissue and left in place, perhaps with a temporary removable cap covering the proximal end 64 and the recessed fixation element therein. The position of the distal part 7b may then be determined, e.g. by CT scanning, providing data for the position in space of the distal portion 7b. Based on this data, amongst other, a surgical template may be produced upon a virtual planning of a dental restoration. The proximal part 7a may then be assembled with the distal part 7b, still in place in the bone tissue, via a guide sleeve of the real surgical template produced from data resulting from the virtual planning. Dental implants may be implanted using the surgical template as guidance for surgical drills providing bore holes for insertion of the dental implants. After this medical procedure is finished, the anchor screw 7 may be removed from the bone tissue. A thread of fixation element 79 may for instance have an opposite thread direction than the threaded section 75. Thus torque applied to the thus transmitting torque applied to the head section 70 of the proximal part 7a is reliably conveyed to the distal part 7b without loosening of the assembly of anchor screw 7.

In addition, the proximal part 7a may be used for releasable fixation to an existing dental implant in a patient. In this case, the fixation element 79 of the connection interface of the proximal part 7a may mate with a standard dental implant connection interface. In this way, the proximal part 7a may provide attachment of a surgical template to an existing dental implant via a suitable guide sleeve in the surgical template.

In embodiments, the apical end sections 57, 67, 77 may comprise a tip that has a conical, frusto-conical, or reduced diameter shape in relation to the maximum outer diameter of the thread 55, 65, 75, respectively. The tip proximally adjoins a cylindrical section adjoining the distal end of thread 55, 65, 75, respectively. The cylindrical section has approximately a diameter corresponding to a diameter of a bore into which the thread 55, 65, 75, respectively are intended to be inserted. This diameter is also chosen as the diameter at the thread bottom of the threaded sections 55, 65, 75 respectively. The apical ends 57, 67, 77 may comprise a rounded tip. In this manner, a secure and safe insertion into a bore is provided, as the apical end serves as a pathfinder for the insertion of the threaded sections 57, 67, 77 into the bore. When the treaded section thus is inserted into a bore, a secure fixation in the bone tissue is achieved.

Anchor screw 5, temporary anchor implant 6, or anchor screw 7 are not intended for permanent implant in the bone tissue. They will be removed from the bone tissue after a certain time period. Osseointegration with the surrounding bone tissue is not desired and anchor screw 5, temporary anchor implant 6, or anchor screw 7 are not adapted for providing osseointegration.

Dental implants, on the contrary, are intended to be osseointegrated upon implantation.

In some embodiments, one or more existing dental implants may be used as reference structures that are fixed in the patient. In case the patient previously has been provided with one or more dental implants, these may be used in embodiments of the present method. The position in space of the implants may be registered and provided in a first input data, based on which a first set of data may be generated.

As mentioned above, a first input data is generated of the patient situation as depicted in FIG. 3. The first input data set comprises data for the position in space of the reference structure, i.e. in the present embodiment of the temporary anchor implant 6. The first input data set comprises in this present embodiment also data for the position of the master structure, determinable via the positions of the gutta percha markers of the radiographic guide 2 in the first data set. In this manner a defined relation between the reference structure, the master structure and the bone tissue is determinable from the first data set. However, in order to provide a practically implementable virtual planning, it may also be necessary to provide a second input data set for the master structure, e.g. providing data for portions that are non-radiopaque and do not provide useful data for generating the first data set based on the first input data.

Input data sets comprising digitized patient data for a computer based virtual planning of a medical procedure may be generated in various manners, including:
- 3D data—provided from scanning an impression or a cast model of a body portion of the patient, e.g. using touch probe scanners or optical scanners.
- Patient data from imaging modalities, such as CT, MR, X-ray, Ultrasound, including Orthopantomograms (OPGs)
- 2D and 3D photographies.
- 3D skeletal and/or skin models.

An OPG is a panoramic scanning dental X-ray of the upper and lower jaw, basically providing a two-dimensional view of a half-circle from ear to ear.

According to the double-scan technique, two CT scans are performed: (1) a first patient CT scan with a radiographic guide and a radiographic index as well as a reference structure in the patient providing a first input data; and (2) a second CT scan of the radiographic guide only without the radiographic index, providing second input data. Since the Hounsfield Units generated for the radiographic guide resemble so closely those of soft tissue, the double-scan is used to extract the radiographic guide from a single CT scan.

The purpose of the double-scan is to get clear and precise data of the patient's alveolar bone tissue (first scan), the reference structure fixated to the bone tissue (first scan), and detailed data of the radiographic guide (second scan). The gutta percha markers on the radiographic guide may be used as reference points to perform an accurate data merger or data association of input data generated by each of the both scans.

Matching of several CT scans may be made according to the Dual Scan technique provided by the NobelGuide® concept. As mentioned above, it is for example used for matching a radiographic guide with patient data.

Another matching technique for matching data from different input sources is for instance described in patent application PCT/EP2007/050426, filed on Jan. 17, 2007, of the same applicant as the present application, which is incorporated herein by reference in its entirety. Such data may be provided as a first input data set and/or a second input data set.

From the digitized patient data, including the first input data and the second input data, a virtual treatment planning of a surgical procedure at a cranial site of a body of a patient is performed. This patient treatment planning allows for a design and product customization of products to be used in the surgical procedure. In this manner, data is provided for production of such medical products, such as implants, prosthesis, membranes for casting bone replacement material, surgical templates, cutting templates, surgical templates for drill and implant guided surgery, guiding templates for distraction procedures, etc. Products may comprise provisional bridges, frameworks for bridges, final bridges, copings, abutments, surgical templates, bone prosthesis, 3D bone anatomical implants, membranes, etc.

Based on this data, the products may be produced and used for performing a real surgical procedure based on the virtual planning thereof.

In order to virtually plan a desired final result of a real medical procedure, several tools may be used, such as for instance a library of virtual teeth; an image of a body portion, such as a face; a virtual articulator such as described in WO95/22299 of the same applicant as the present application, which is incorporated herein by reference in its entirety; simulations of implant positions for providing data for a surgical template for drill and implant guided surgery, or a cutting template; etc. By means of such tools a desired final result of a medical procedure may be virtually determined or verified.

Hence, a present anatomical situation of the patient is known, e.g. based on patient input data, e.g. from imaging modalities, such as CT, MR, or impressions of body portions of the patient that are scanned, as explained above. The final result of a medical, i.e. surgical procedure is virtually planned, and may for instance be presented on a display of a medical workstation. The virtual planning may provide data to be used for producing medical products used in the medical procedure. In this manner, a real medical procedure may be performed based on the virtual planning thereof. During the real medical procedure the medical products may be used, which are produced based on the data of the virtual planning and or the input data.

In the present context the virtual planning of dental restorations is not described in more detail. A detailed description is e.g. given in the references cited above, which are incorporated herein by reference in their entirety. In the present context a focus is made on providing input data for a virtual planning of virtual surgical templates, and from said virtual planning providing data for production of corresponding real surgical templates.

Figure 5:
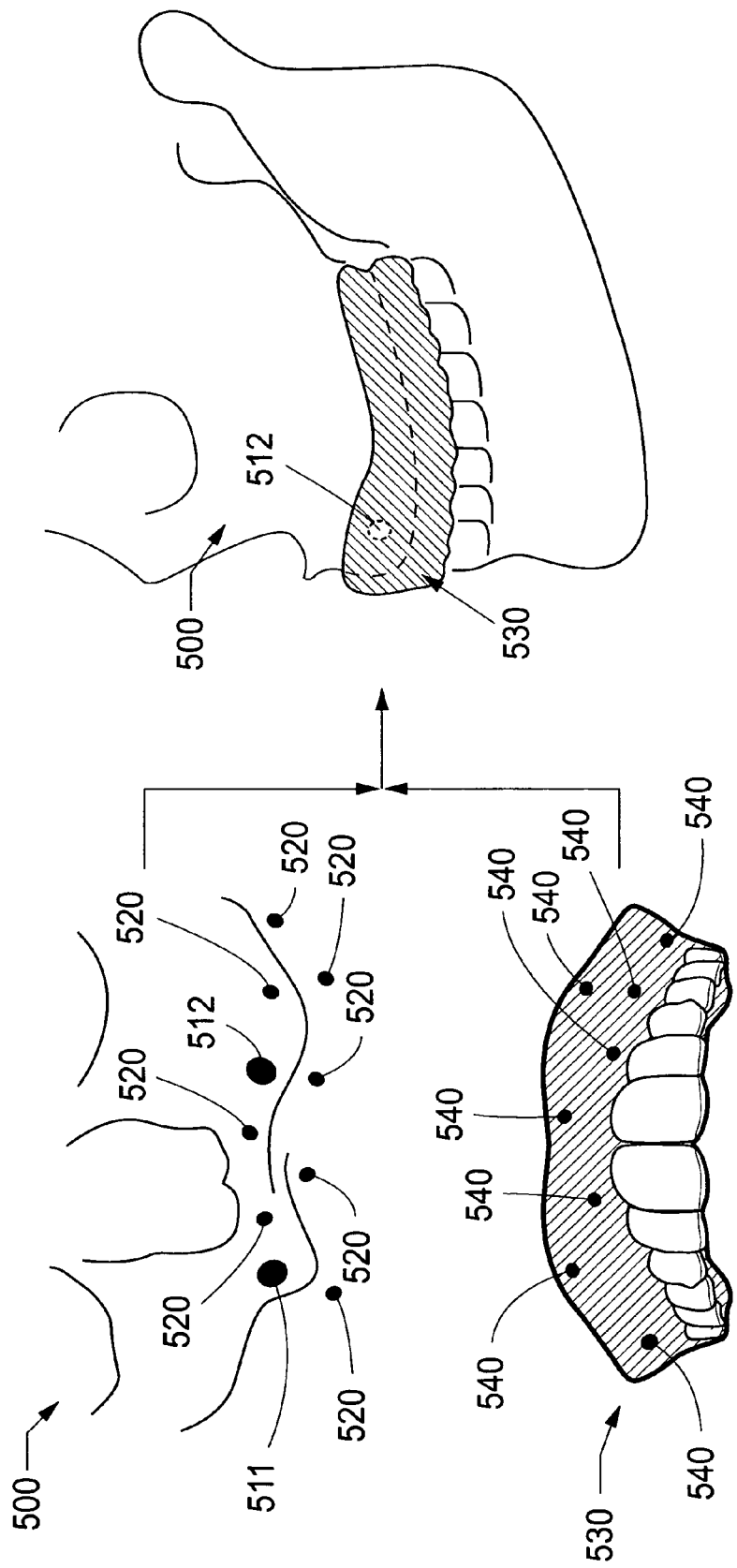
FIG. 5 is a schematic illustration of associating two 3D data files in a common cranial coordinate system in virtual planning by means of a temporary anchoring implant.

FIG. 5 is a schematic illustration of associating two 3D data files in a common cranial coordinate system in virtual planning by means of a temporary anchoring implant.

For generating the first data set, based on the first input data, the position and direction of the temporary anchoring implant are located, e.g. by suitable algorithms, such as surface detection, object recognition, etc. For instance a voxel based matching may be performed in input image data, such as the first input data, i.e. a shape and/or density based identification may for instance be performed, providing a position and direction of a temporary anchor implant or an anchor screw.

In the illustrated example, two temporary anchor implants 6 are screwed into the maxilla 300. The first input data set comprises data for the position of the gutta percha markers 520 and the temporary anchor implants 511, 512 in the cranium 500, as e.g. visualized on a screen of a medical workstation, such as shown in FIG. 5 on the left top side.

The first input data comprises also positions of the gutta percha markers 540, but in relation to the remaining data of the data set, representing the radiographic guide 530, such as shown in FIG. 5 on the left lower side.

The separate first and second 3D data files are aligned by matching the gutta percha markers 520, 540 in both data sets in a common coordinate system, resulting in a common data set, as shown in FIG. 5 on the right side. The first and second data sets are associated with each other such that a relation of the reference structure, i.e. the temporary anchor implant 6, to the master structure, i.e. the radiographic guide 2, is preserved.

Figure 6:
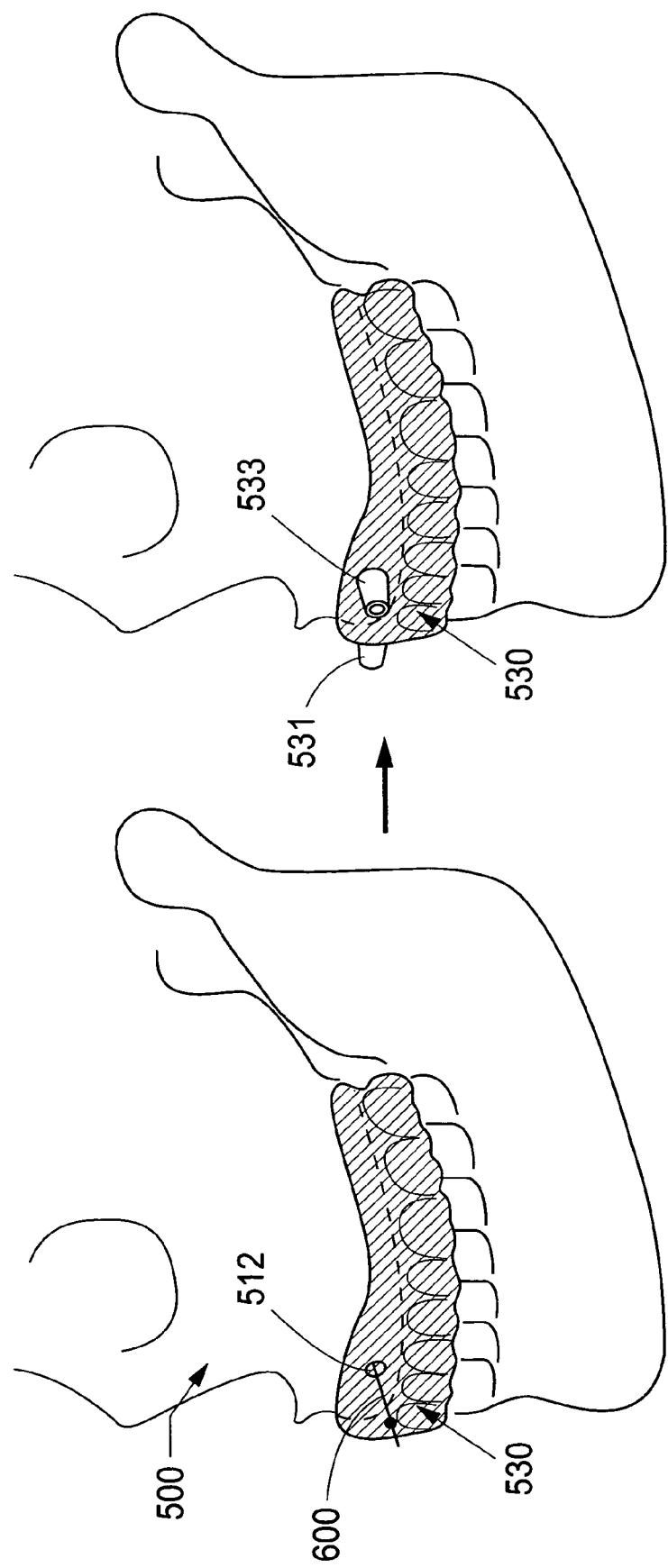
FIG. 6 is a schematic illustration of positioning a surgical template anchoring sleeves in virtual planning by means of a temporary anchoring implant position.

FIG. 6 is a schematic illustration of positioning a surgical template anchoring sleeves in virtual planning by means of a temporary anchoring implant position. The temporary anchoring implants positions are used to virtually plan and position at least one sleeve for an anchoring device, such as the anchoring screw 5 described above. In the example, a first anchoring sleeve 531 is planned from the position and direction of the first temporary anchor implant 511, and a second anchoring sleeve 533 is planned from the position and direction 600 of the (in this exemplary embodiment) second temporary anchor implant 512.

The first input data set comprising the position in space of reference structures, i.e. a position and direction thereof, may be obtained in various ways from the first input data set. For instance, a position in space of a reference structure may be identified in the first input data set, based on a comparison with a predefined shape or density thereof, whereby the first input data comprises said position in space. In more detail, a CAD object database may for instance comprise data for the shape, density and/or dimensions of components used in dental restorative procedures. These components may comprise the reference structures used in the present method, e.g. temporary anchoring implants, existing standard dental implants, anchor screws, proximal and/or distal parts of two-part anchor screws, etc. Identification of the component may thus for instance be provided upon a matching comparison of the shape or density of objects in the first input data and the CAD object database. For example a search is made in the first input data set for a reference structure matching a component of the object database.

The predefined shape may be an asymmetrical shape in a longitudinal direction of the reference structure. Thus, by identifying the predefined shape of an object in a data set, the position in space, including the orientation thereof, may be determined based on the asymmetrical shape. For instance a component, such as an anchor screw 5 or a temporary anchoring implant 6, may have different diameters at the apical part and collar thereof, which facilitates identification of the direction and orientation of the component by the above described comparison of objects.

Identification may be done by identifying a portion of a component, e.g. an asymmetrical shape of a coronal part of a dental implant or of a temporary anchoring implant. Upon identification of such a portion of a component the remainder of the shape of that component may be added from the CAD object database. In this manner data for the complete component is provideable, which may be used in virtual planning of a dental procedure. From the complete component the first data set may be generated.

The identification may be implemented as an object identification module. The object identification module may provide an identification of a component and/or a position in space (position, direction and orientation) thereof in a 3D data set. The component may be a reference structure, as described herein.

The object identification module may use any input data set that comprises data for a reference structure, such as an anchor screw, a temporary anchoring implant, or an existing implant. The input data set may be generated by various data generating modalities, such as a CT scanner, intraoral scanner, etc.

The object identification module extracts from this input data set the position in space of the reference structure and/or identifies the type of reference structure.

The object identification module may be voxel based, wherein a suitable algorithm searches for a density and shape for the identification of the object. The search may be based on a comparison with components in the CAD object database. Upon a match of the compared density and/or shape, a position in space of the component is provided by the object identification module. The density and/or shape may be of an entire reference structure or of a portion thereof.

In addition, or alternatively, the object identification module may be based on identification of fiducial markers that are attached to or integrated with a reference structure.

The object identification module may send, export or provide output data for the identified component to a software product for virtual planning of surgical procedures. The object identification module may comprise external, separate, or integrated code segments of the software product for virtual planning of surgical procedures.

Generating the first data set may comprise matching at least a portion of an anchoring element with a corresponding portion of the reference structure. The anchoring element may be an anchoring screw or a fixation element for fixation to a reference object. This may comprise a template abutment for fixation to an existing dental implant; or the proximal part 7a of the two-part anchor screw shown in FIG. 4D, and an existing dental implant or the distal part 7b of the two-part anchor screw of FIG. 4D. This may increase accuracy of the method.

In addition or alternatively, a shape of a reference structure may be extracted from the first input data. The shape may be compared to elements of a library of predefined virtual components (e.g. CAD components). When a match of similar shapes is detected, a position in space of the matched reference structure may be obtained.

Further anchoring sleeves may be planned in addition, such as the third anchoring sleeve 532 shown in FIG. 7. FIG. 7 is a schematic illustration of design and production of said surgical template from data provided from said virtual planning. The virtually template 530 is provided with guides 535, 536, 537, 538 for allowing directed drilling and insertion of dental implants. Dental implants may comprise standard dental implants and/or zygoma implants for fixation in zygomatic bone tissue (cheek bone tissue). In particular when planning a drill and implant guided dental surgery with one or more zygoma implants, a correct positioning as provided by the invention is of advantage. A critical factor is that a substantially longer drill is used for drilling a hole into bone tissue, into which hole a zygoma implant is to be implanted, than for conventional dental implants. Therefore it is of particular importance that the surgical template comprising the guide sleeve for guiding the drill into the correct direction is correctly positioned. For instance, it may occur that certain patients need two zygoma implants per side for providing suitable fixation to a dental restoration. Embodiments of the invention provide a secure and accurate positioning of the surgical template in place, thus facilitating critical applications, such as implantation of one or more zygoma implants.

In other embodiments non-dental implants may be virtually planned, such as ear implants, based on corresponding input data.

From the associated first data set and second data set, a third data set for production of a real surgical template 730 is provided. The real surgical template 730 may thus be produced comprising real anchoring sleeves 731, 732, 733 and real guides 735, 736, 737, 738, corresponding to the virtually planned anchoring sleeves 531, 532, 533 and guides 535, 536, 537, 538. Production of the real surgical template 730 may for instance be done by rapid prototyping techniques.

Figure 8A:
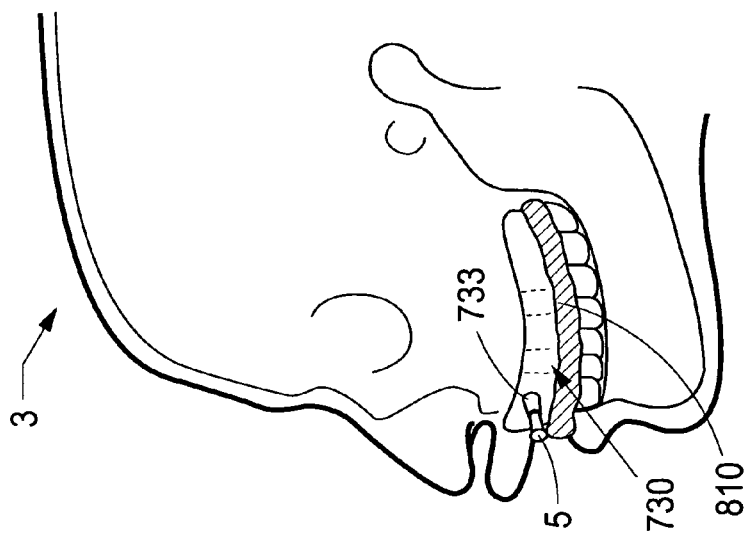
FIGS. 8A, 8B, 8C are schematic illustrations of removing a temporary anchoring implant, a threaded drill channel in a maxilla of the subject, and a mounted surgical template and surgical index in the oral cavity of the subject, respectively.
Figure 8B:
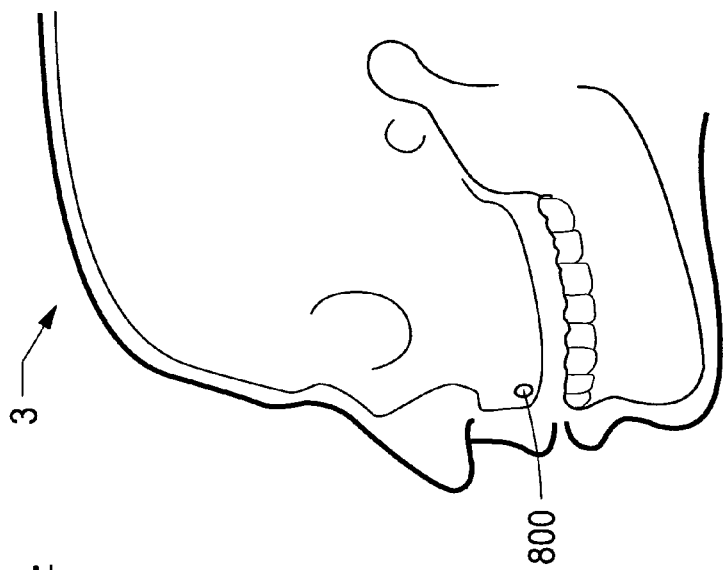
Figure 8C:
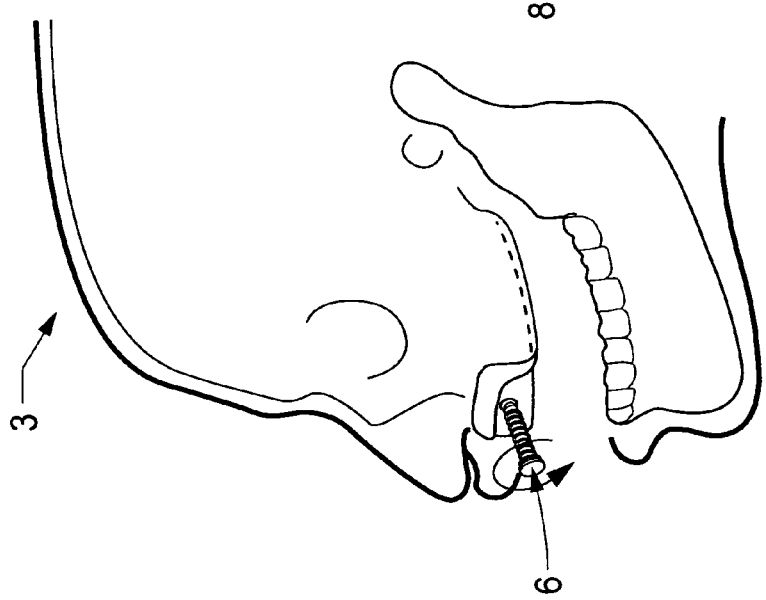

Having the thus produced real surgical template 730 available, the temporary anchoring implant 6 is removed from the subject, as illustrated in FIG. 8A. FIGS. 8A, 8B, 8C are schematic illustrations of removing a temporary anchoring implant, from its position, as shown in FIG. 3. A threaded bore 800 is now present in the bone tissue of the maxilla. When inserting the real surgical template 730 into the oral cavity of the subject, it is fixed and positioned correctly by inserting an anchor screw 5 through the anchor sleeve 733 into the threaded bore 800. A pre-positioning of the surgical template may be made by means of a surgical index 810, before locking the surgical template in the correct position by means of the anchor screw 5.

Further anchor screws or anchor pins may be introduced through remaining anchor sleeves into the jaw bone tissue, thus further improving the stability of the surgical template 730 in the oral cavity.

Now the surgical implant is in a correct position for drilling and insertion of dental implants by using guides 535, 536, 537, 538.

Figure 9B:
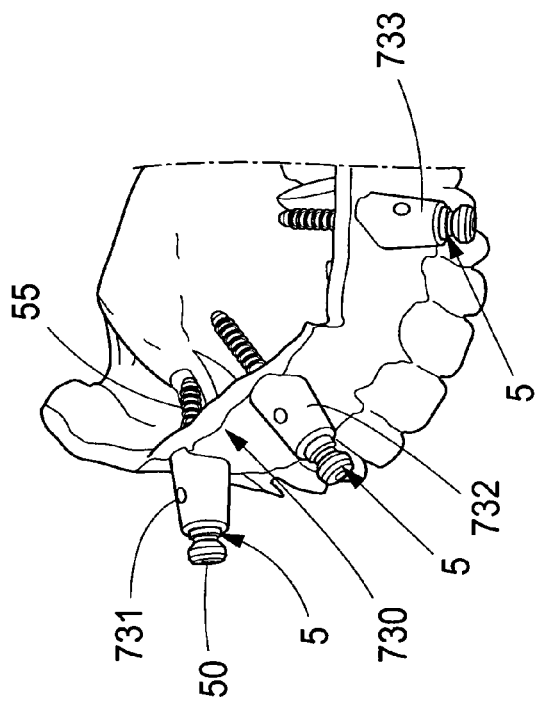
FIGS. 9A, 9B, 9C are elevated perspective views of a surgical template, the surgical template with three anchor screws, and the surgical template with an anchor screw and two anchor pins, respectively.
Figure 9C:
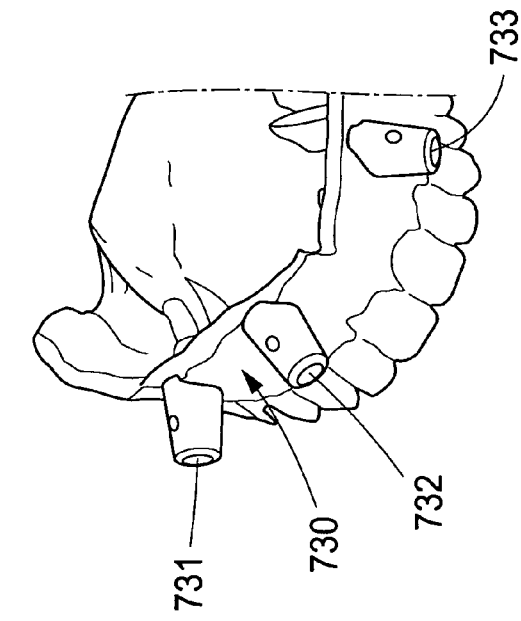
Figure 9A:
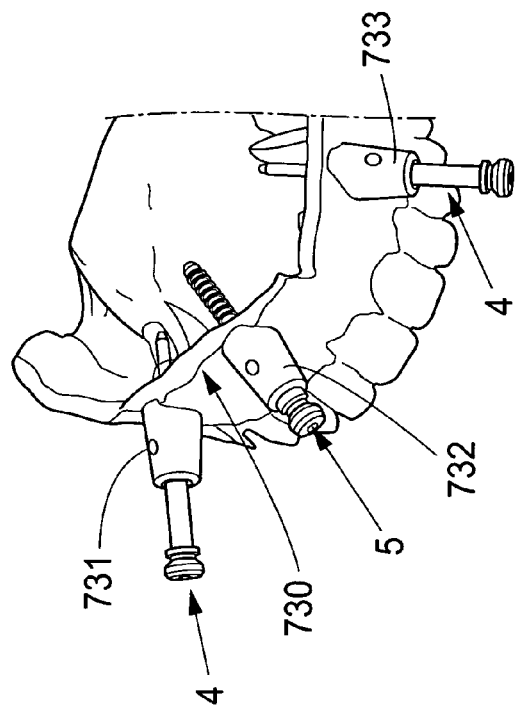

In FIG. 9A a surgical template 730 is shown.

Some examples of virtual planning anchoring a surgical template 730 are given in FIGS. 9B and 9C.

In FIG. 9B three anchoring screws 5 are shown introduced through anchoring guide sleeves 731, 732, 733. In FIG. 9C, one temporary anchoring implant 5 is inserted into anchoring guide sleeve 732, wherein the remaining anchoring guide sleeves 731, 733 receive anchoring pins 4.

In FIGS. 9B and 9C, it is illustrated how production data for a surgical template is provided based on virtual planning. Components, such as anchor screws 5 or anchor pins 4 are virtually positioned at desired or suitable positions. Anchor screws 5 for instance may be positioned at the position of reference structures, such as anchor screws that are present inserted through the radiographic guide upon generating the first data set. Implants may be positioned at suitable locations. The shape of the radiographic guide is adjusted in order to provide production data for the surgical template. Boundary surfaces of known components are for instance used for defining matching boundary surfaces of the surgical template. For instance guide sleeves are positioned at suitable positions and with suitable orientations, stop boundaries, etc. in the surgical template to provide a guide for anchor screws, anchor pins, surgical drills and implants, template abutments for fixation to existing dental implants, etc.

Production data for a surface of a surgical template may directly be provided from data of a bone structure or soft tissue. For instance, CT scanning may provide second input data for a bone structure, such as a jaw bone. The CT scanning generates in addition first input data for a reference structure, wherein even the second input data is provided in the first data set. Hence, both data for the reference structure and the bone structure are provided in a defined relation in a single data set, namely the first data set. Based upon this input data, production data for a real surgical data may be provided without the need for a radiographic guide. The initial form of the virtual surgical template may be the exterior surface of the bone structure itself. From this initial data, the shape of the virtual surgical template is adjusted in order to provide the second data set for associating with the first data set for providing production data (third data set) for the real surgical template. Boundary surfaces of known components are for instance used for defining matching boundary surfaces of the surgical template. For instance guide sleeves are positioned at suitable positions and with suitable orientations, stop boundaries, etc. in the virtual surgical template to provide a guide for anchor screws, anchor pins, surgical drills and implants, template abutments for fixation to existing dental implants, etc. Based on the data of the virtual surgical template, a real surgical template may be produced for use in a real surgical procedure.

Production data for a surface of a surgical template may in a corresponding manner directly be provided from data of a soft tissue structure. The second input data for the second data set comprising the data for the soft tissue structure may be provided from suitable data sources, such as MR imaging; ultrasonic imaging; optical imaging, such as Optical Coherence Tomography; manual probing for determining layer thickness profiles of soft tissue; etc.

In addition or alternatively, an at least partly radiopaque radiographic guide may provide the second input data directly in a single patient CT scan together with the first input data. For this purpose, the radiographic guide may at least partly be provided with a coating of radiopaque material, or be provided with a layer of a radiopaque paint, e.g. barium sulfate acrylic paint. A radiographic guide may also be produced from a radiopaque material, such as a mixture of barium sulfate and acrylic resin, providing a radiopaque radiographic guide.

In this manner a position of the radiographic guide may be identified in CT scan data without the need of providing separate fiducial markers (e.g. gutta percha markers) on the radiographic guide. A double scanning technique may thus not be necessary. However, in practice a metal object in the scan structure such as dental fillings, metal bridges, copings, etc. may lead to streak artefacts rendering the generated data unsuitable for a precise virtual planning of a surgical procedure and subsequent production of components based on the virtual planning. These artefacts may cause serious problems during the virtual planning as they may obscure the dental arches in the CT scan, as for it may be impossible to distinguish between the radiopaque material including barium sulfate in the radiographic guide and the streak artefacts.

In other embodiments additional or other reference structures may be used for providing first input data in accordance with the above described principle for repositioning purposes, such as existing dental implants or other anatomical landmarks.

For instance, existing implants in the patient may be used as reference structures in the first input data set for providing position and orientation thereof for generating the first data set. For instance, one or more existing dental implants may be used for locking a radiographic guide to the dental implants by means of template abutments. The real surgical template produced from production data (third data set) provided in accordance with the above described virtual planning method, may the also be locked into the correct position by means of such template abutments interlocking to the existing dental implants during the surgical procedure to be performed. Hence, in some embodiments, the first data set may be directly based on the position of the existing dental implant (s) in the first input data set. The first data set comprises data for the template abutments suitably arranged in the radiographic guide, providing data for producing a surgical template to be locked to the existing implant(s) in the desired re-positioned arrangement during the surgical procedure. In this embodiment the surgical template is produced from data of a radiographic guide that is modified based on the position in space of the dental implant and a connection interface thereof. A guide sleeve is provided in the surgical template for guiding the template abutment towards the connection interface and upon locking of the template abutment to the dental implant, e.g. by threadably locking, the surgical template is locked in the correct position. A stop shoulder is provided suitably in the guide sleeve channel to provide a tight fit of the template abutment to the dental implant and thus of the surgical template to the dental implant.

A further embodiment of the invention is illustrated in FIGS. 10 to 13. In correspondence with the embodiments described above with reference to FIGS. 2 to 9, similar steps and units are not repeated in detail.

Figure 10:
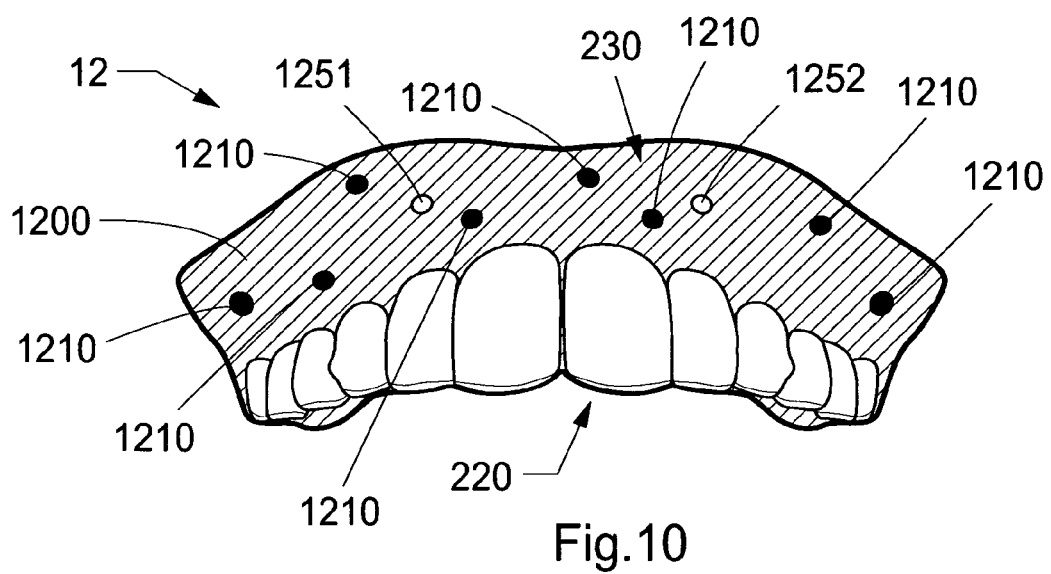
FIG. 10 is perspective view of another radiographic guide.

In FIG. 10 a radiographic guide 12 is shown comprising a plurality of radiopaque fiducial markers 1210, e.g. spherical markers produced of gutta percha for CT scanning. The radiographic guide 12 further comprises through holes 1251, 1252 for insertion of anchor screws. In other embodiments only one through hole, or more than two through holes are provided. The number of through holes may for instance be chosen depending on the specific anatomical situation of the subject, existing implants or other landmarks available.

The through holes may be provided at suitable positions when producing the radiographic guide. Alternatively, the through holes may be drilled in the radiographic guide when the radiographic guide is fit into the subject, either when in place in the subject or suitable positions may be marked when it is in place in the patient and the through holes may be drilled after removing the radiographic guide from the subject. Alternatively anchor screws 5 with self tapping threads may be used for direct insertion in to the radiographic guide 12 and into adjacent bone tissue, thus creating the through holes in the same step as the radiographic guide is fixed into position prior to the first CT scan.

Figure 11:
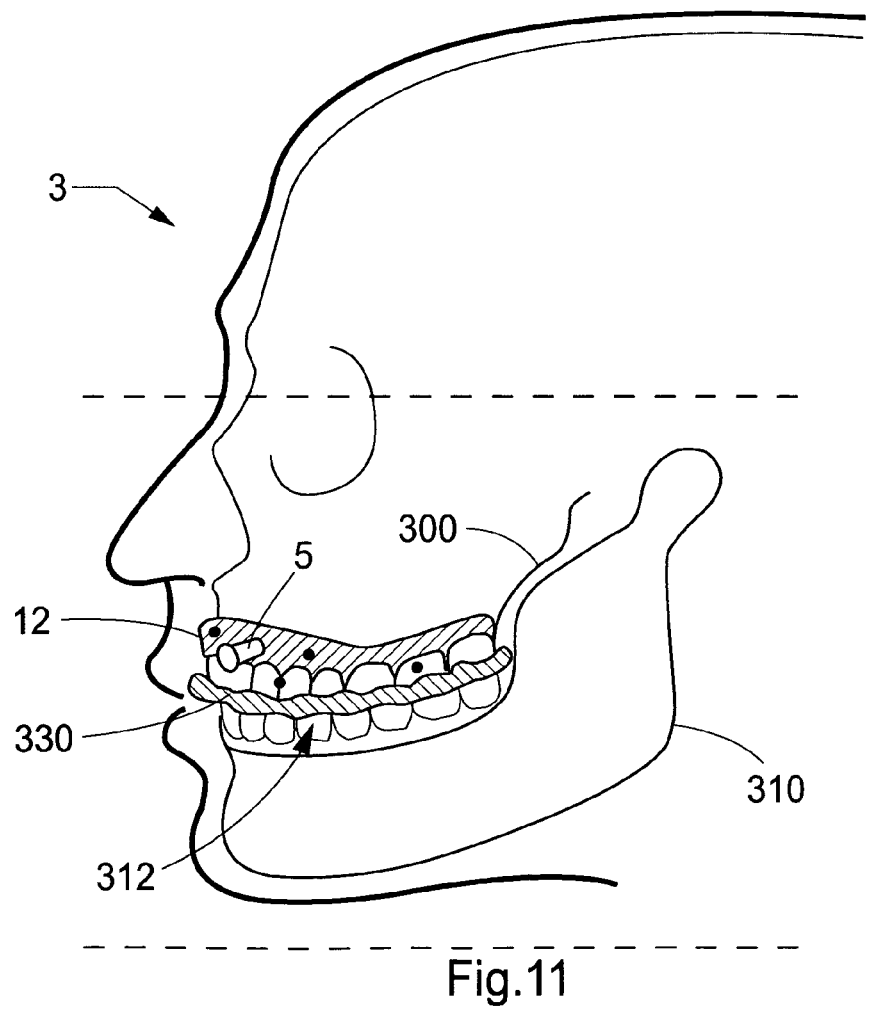
FIG. 11 is a schematic view of the cranial region of a subject with a radiographic guide, a bite index and an anchor screw.

FIG. 11 shows a subject with the radiographic guide 12, a radiographic index 330, and an anchor screw 5 inserted into the through hole 1252 and fixated into the maxilla 300. Another anchor screw 5 is inserted into the through hole 1251 (not shown) in a corresponding manner. Thus the radiographic guide is securely fixed in position for registering a first input data set comprising both the position of the gutta percha markers 1210 and the anchor screws 5 in relation to the maxillary bone tissue.

When the first CT scan is finished, the anchor screws 5 are removed from the jaw bone tissue and the radiographic guide is removed from the patient for the second CT scan. A temporary anchoring screw is inserted into the threaded bore left behind by the anchoring screw until the medical procedure continues with inserting dental implants by means of a real surgical template, as described above with reference to FIGS. 8 and 9.

Figure 12:
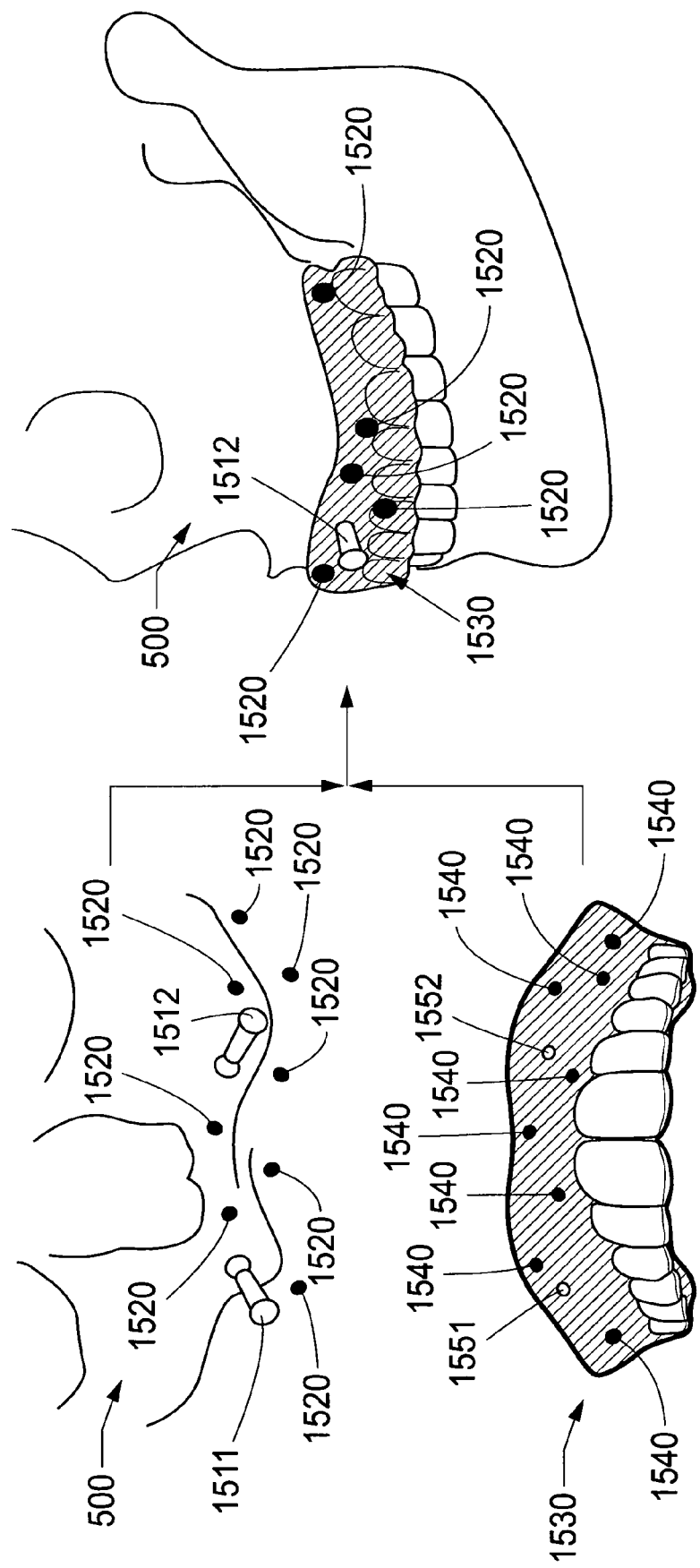
FIG. 12 is a schematic illustration of associating two 3D data files in a common cranial coordinate system in virtual planning by means of an anchoring screw.

FIG. 12 is a schematic illustration of associating two 3D data files in a common cranial coordinate system in virtual planning by means of at least one anchoring screw having a defined position and orientation, as described above with reference to FIG. 5. Here, two anchor screws 5 are screwed into the maxilla 300 via the through holes in the radiographic guide. The first input data set comprises data for the position of the gutta percha markers 1520 and the anchor screws 1511, 1512 in the cranium 500. The second input data set comprises also positions of the gutta percha markers 1540, but in relation to the remaining data of the data set, representing the radiographic guide 1530.

Figure 13:
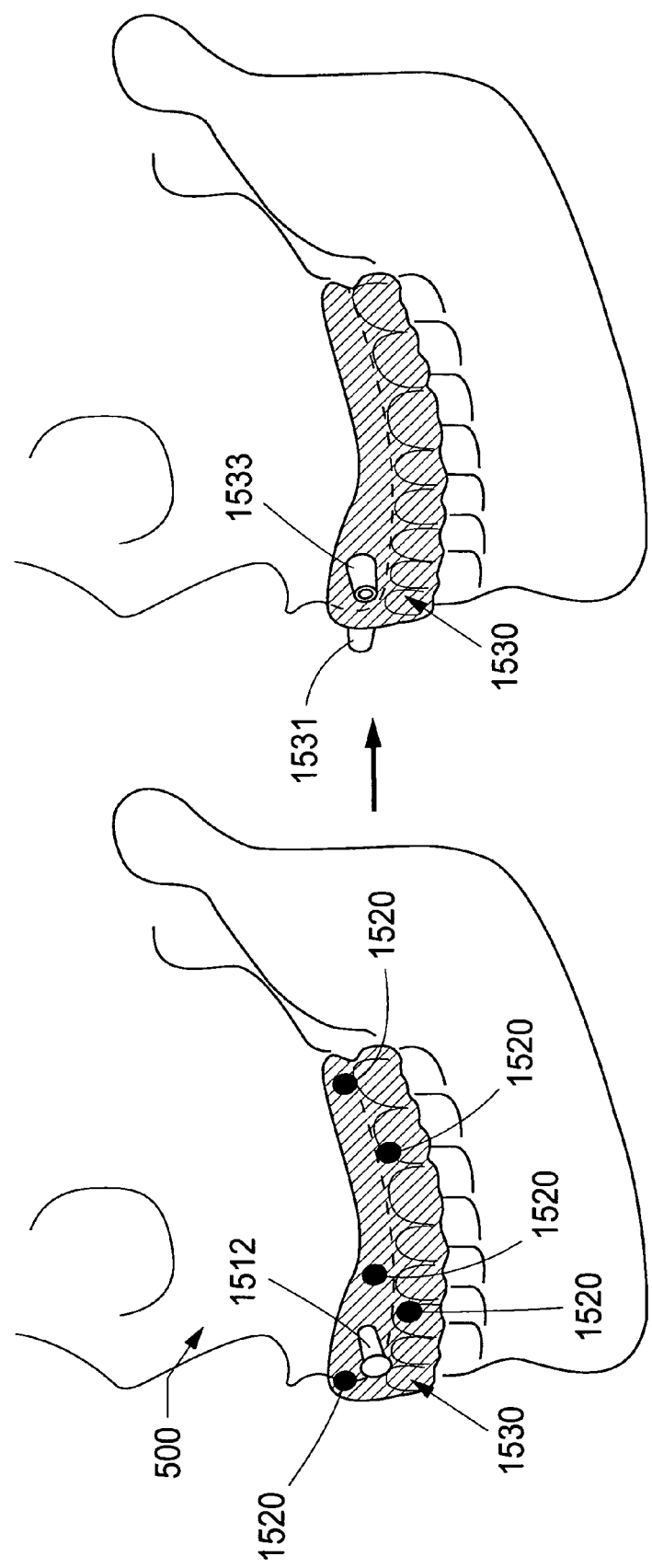
FIG. 13 is a schematic illustration of positioning a surgical template anchoring sleeves in virtual planning by means of the position of an anchoring screw.

In FIG. 13 additionally, a first anchoring sleeve 1531 and a second anchoring sleeve 1533 are shown, wherein data for these sleeves is based on the first input data (planned from the position and direction of the first and second anchor screws 1511, 1512).

Figure 14:
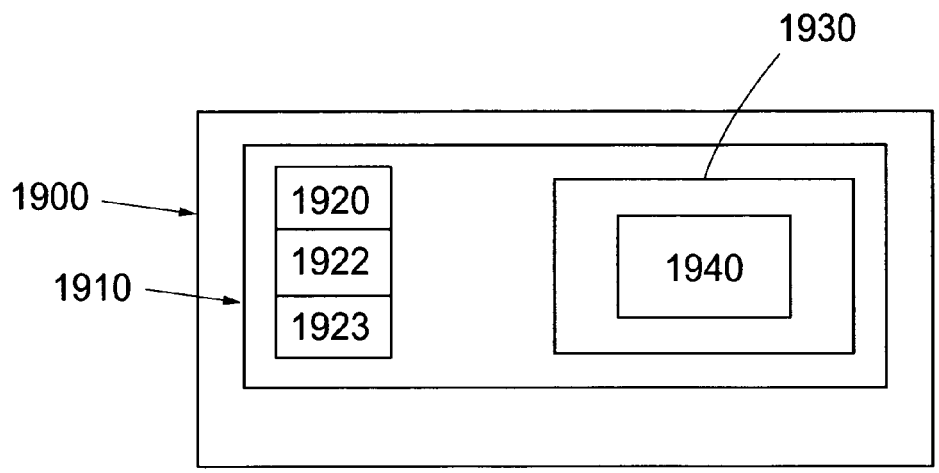
FIG. 14 is a schematic illustration of a system for virtually planning a cranial drilled implant guided surgery.

FIG. 14 is a schematic illustration of a system for virtually planning a cranial drilled implant guided surgery. A presurgical planning of the medical procedure may be performed virtually in a computer based environment. The presurgical planning may be made automatically or in an interactive way with a user. Planning of the dental restoration may in the latter case be made visually on a display of a medical workstation, e.g. of the system described below with reference to FIG. 14, in an interactive way manipulated by user input. For instance the position and direction of dental implants in jaw bone is virtually presented on the display visualizing the jaw bone structure where a dental restoration is to be made. During planning care has to be taken that for instance no nerves are damaged or that the dental implant is positioned in as much dense bone as possible, in order to ensure a successful surgical installation of the dental implant. Hence, the user may virtually manipulate or accept placement of dental implants in advance of final placement. The implant's position, angulation, type of implant, length, in relation to final teeth restoration, may in an interactive manner be manually fine tuned.

When the implant is virtually positioned, a fixed outer boundary surface of the implant, or a boundary surface of an abutment that is to be attached to the implant, is determined. Now the intermediate structure between the implant and the veneering will be provided in order to finalize planning of the dental restoration.

The system 1900 provides computer-based planning of a cranial surgical procedure of a patient. The system 1900 comprises a unit 1922 for virtual planning of a cranial drilled implant guided surgery of a patient; and a unit 1923 for generating data based on said virtual planning, wherein said data is configured for subsequent use in production of a real surgical template procedure for said cranial drilled implant guided surgery, and/or for controlling a device configured to facilitate said cranial drilled implant guided surgery.

A medical workstation 1910 comprises the usual computer components like a central processing unit (CPU) 1920, memory, interfaces, etc. Moreover, it is equipped with appropriate software for processing data received from data input sources, such as data obtained from CT scanning or 3D scanning. Software may for instance be stored on a computer readable medium 1930 accessible by the medical workstation 1910. The computer readable medium 1930 may comprise the software in form of a computer program 1940 comprising suitable code segments 190, 191, 192 for performing a virtual planning of a cranial drilled implant guided surgery of a patient. The medical workstation 1910 further comprises a monitor, for instance for the display of rendered visualizations, as well as suitable human interface devices, like a keyboard, mouse, etc., e.g. for manually fine tuning an automatical planning otherwise provided by the software. The medical workstation may be part of the system 1900. The medical workstation may also provide data for producing at least one of a dental restoration and a product related to the dental restorative procedure, such as a surgical template.

A result of the virtual planning may be provided to a user in a graphical user interface on the medical workstation 1910.

For planning, patient data, e.g. from a CT scan, is imported into a software for pre-surgical planning of dental restorative procedures, for instance run on the medical workstation 1910. The medical workstation 1910 may have a graphical user interface for computer-based planning of a dental restorative procedure of a patient having a craniooral space, and/or of at least one dental component for said dental restorative procedure. The graphical user interface may comprise components for visualizing the method described above in this specification or recited in the attached claims.

Figure 15:
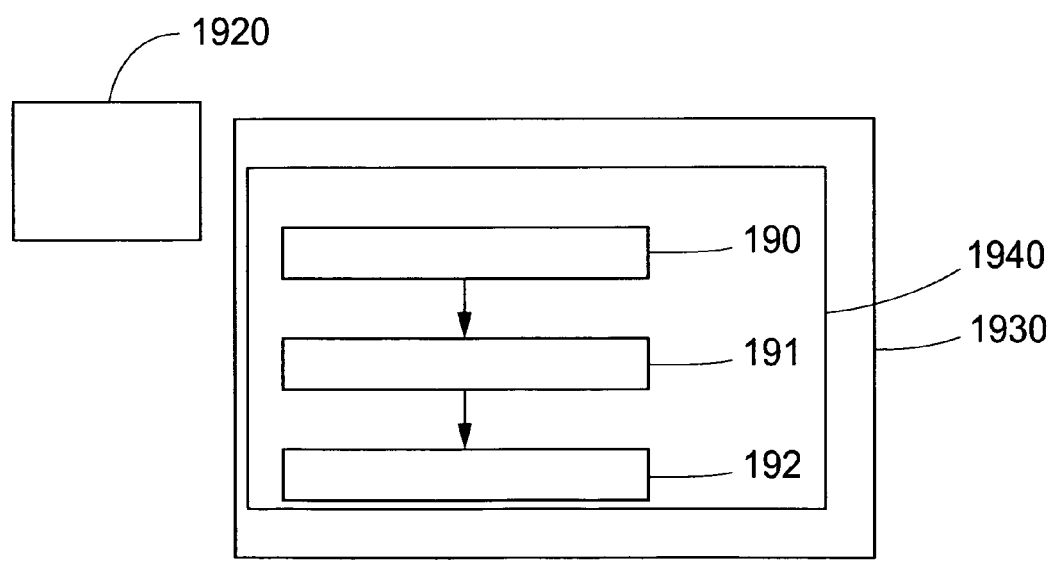
FIG. 15 is a schematic illustration of a computer program for virtually planning a cranial drilled implant guided surgery, stored on a computer readable medium.

FIG. 15 is a schematic illustration of a computer program for virtually planning a cranial drilled implant guided surgery, stored on a computer readable medium. The computer software comprises a first code segment 190 for generating a first data set based on input data obtained from a reference structure having a defined fixed relation to a bone structure of said subject; a second code segment 191 for generating a second data set based on input data obtained from a master structure for a surgical template, said master structure having a defined relation to said reference structure; and a third code segment 192 for associating said first data set with said second data set such that said relation of said reference structure to said master structure is preserved whereby a third data set for production of said Surgical template is provided; wherein said third data set is configured for subsequent use in production of a real surgical template procedure for said cranial drilled implant guided surgery, and/or for controlling a device configured to facilitate said cranial drilled implant guided surgery.

The virtually planning a cranial drilled implant guided surgery may comprise virtually planning of implant anchored facial reconstructions, including ear, nose, and/or eye prosthesis.

A medical method may comprise such a cranial surgical procedure and may comprises anchoring a reference structure, as described above, at a cranial site of a patient; generating data for the method of virtually planning a cranial drilled implant guided surgery, as described above. The cranial surgical procedure may further comprise positioning a real surgical template, that is produced by the method described above, at a site of the cranial surgical procedure, and locking the real surgical template to the reference structure or towards a bore prepared by the reference structure.

EXAMPLES

Below some further non-limiting examples of the computer based method of virtually planning a cranial drilled implant guided surgery in a patient are given.

Example 1 a) A surgeon positions at least one temporary anchoring implant (reference structure) into jaw bone tissue that only a top part of the head section thereof protrudes into the soft tissue.
b) A radiographic guide (master structure) in form of a duplicate prosthesis with gutta percha markers is put into position, and slid over the head section in the soft tissue, such that the master structure has a defined relation to the reference structure.
c) A first CT scan is performed with the patient wearing the radiographic guide and a radiographic index, providing a first set of data. The first scan may be performed with a low dosage CT scanner to minimize radiation impact on the patient.
d) A second CT scan of the radiographic guide only is performed, providing a second set of data.
e) Virtual planning of the dental restoration and medical procedure is performed, providing production data for a surgical template based on an associated data set of said first data set and said second data set.
f) The surgical template is produced from the production data.
g) The real medical procedure, based on the virtual planning, comprises
    a. removing the temporary anchor implant;
    b. putting the surgical template substantially in position, wherein this may be supported by a bite index;
    c. locking the surgical template in position by means of at least one anchor screw inserted via a guide sleeve into the corresponding adjacent threaded bore left by the temporary anchor implant;
    d. dental implants are implanted, by drills and implants guided by guide sleeves;
    e. the anchor screws and the surgical template are removed and the surgical procedure is finalized.

Example 2 a) an OPG of the subject is taken, with radiopaque markers to define reference points in the flange, e.g. two markers positioned at the top edge of the prosthesis in order to identify position of jaw bone tissue in relation to the prosthesis
b) the prosthesis of the patient is duplicated, e.g. from an impression made thereof providing a form for casting in a cold acrylic material, providing a duplicate prosthesis for use as a radiographic guide
c) either at least one anchor screw are provided in the radiographic guide, via corresponding through holes thereof, or at least one temporary anchor implant is screwed into jaw bone tissue at a suitable position thereof, and the radiographic guide is suitably matched to possible protruding parts of the proximal end of the temporary anchor implant by creating suitable recesses in the radiographic guide, such that it fits into place over the protruding part Alternatively, or in addition to step a) described above, bone position in relation to the radiographic guide may be determined by probing through the soft tissue.

Example 3 a) at least one temporary anchor implant is inserted into jaw bone tissue of a patient
b) a dental impression of the patient is made with a triple tray
c) A CT scan is made of the patient wearing the triple tray and the dental impression therein, wherein the triple tray is provided with fiducial markers, e.g. of gutta percha—providing a first data set for the position and direction of the temporary anchor implant as well as the dental impression in relation thereto d) the dental impression is converted to a second data set, e.g. by means of a 3D scanner, such as a touch probe scanner or an optical scanner, wherein the position of the fiducial markers is provided by a suitable geometrical form thereof, which is registered by the 3D scanner e) the first and second data set are associated as described above, providing a third data set for production of a surgical template.

In case the temporary anchor implant or anchor screw is provided at a position where an implant is to be positioned, other implants may be installed in the first place, then the temporary anchor implant or anchor screw is removed before installing the dental implant at that position.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A computer-implemented method of virtually planning a cranial guided surgery in a subject, said method comprising
   virtually planning a position for an anchoring sleeve of a surgical template with one or more computer processors, based on a position of an artificial physical reference structure positioned on said subject having a defined fixed relation to a bone structure of said subject, wherein said artificial physical reference structure is a temporary anchoring implant,
   generating a first data set based on said virtually planned position for the anchoring sleeve and based on input data obtained of said artificial physical reference structure,
   generating a second data set based on input data of a master structure for said surgical template, said master structure having a defined relation to said artificial physical reference structure, and
   generating a third data set for production of said surgical template based on the first data set and the second data set, wherein the relation of said artificial physical reference structure to said master structure is preserved.

2. The method of claim 1, wherein said master structure comprises at least one structure that is selected from a group consisting of a radiographic guide, a dental impression, and a portion of the subject's actual anatomical situation.

3. The method of claim 1, wherein said second data set comprises a surface model of the master structure.

4. The method according to claim 1,
   wherein said master structure comprises at least one structure selected from a group consisting of a radiographic guide comprising radiopaque fiducial markers, a radiographic guide comprising a radiopaque structure, a radiographic guide comprising a radiopaque material, and a surface of an existing anatomical structure of said subject at a site of the virtually planned surgical procedure.

5. The method of claim 1, comprising:
   identifying a position in space of said artificial physical reference structure based on at least a portion of a predefined shape or density thereof, whereby said first data set comprises said position in space.

6. The method according to claim 5, wherein said predefined shape is an asymmetrical shape in a longitudinal direction thereof.

7. The method according to claim 1, wherein said generating said first data set comprises matching at least a portion of an anchoring element with a corresponding portion of said artificial physical reference structure.

8. The method according to claim 1, wherein said generating said first data set comprises surface matching based on a structure of said artificial physical reference structure and a component from a library.

9. The method according to claim 1, wherein said generating said first data set comprises:
   extracting a shape of said artificial physical reference structure from the first data set,
   comparing the shape to elements of a library of predefined virtual components, and,
   when there is a match of similar shapes, obtaining a position in space of the matched artificial physical reference structure.

10. The method according to claim 1, wherein said generating a third data set for production of said surgical template comprises putting the first and the second data set in a common coordinate system.

11. The method of claim 1, further comprising: producing a real surgical template comprising the method of any of the previous claims for virtually planning a cranial drilled implant guided surgery comprising providing a data set for production of said real surgical template based on said virtual planning, and
   producing a real surgical template based on said third data set for production, wherein said real surgical template is devised for use in a real cranial drilled implant guided surgery corresponding to said virtually planned cranial drilled implant guided surgery.

12. A system for computer-implemented virtually planning a cranial drilled implant guided surgery of a patient, said system comprising one or more computer processors, said one or more computer processing processors being configured to provide:
   a unit for virtual planning of a cranial drilled implant guided surgery of a patient; and
   a unit for generating data based on said virtual planning, wherein said unit for generating data based on said virtual planning comprises
   a unit for virtually planning a position for an anchoring sleeve of a surgical template with said one or more computer processors, based on a position of an artificial physical reference structure on said patient having a defined relation to a bone structure of said patient, wherein said artificial physical reference structure is a temporary anchoring implant, a pre-existing implant, or an anchoring pin or screw,
   a unit for generating a first data set based on said virtually planned position for said anchoring sleeve and based on input data obtained from said artificial physical reference structure,
   a unit for generating a second data set based on input data obtained from a master structure for said surgical template, said master structure having a defined relation to said artificial physical reference structure, and
   a unit for generating a third data set for production of said surgical template based on the first data set and the second data set, wherein the relation of said artificial physical reference structure to said master structure is preserved.

13. The system of claim 12, wherein said master structure comprises at least one structure that is selected from a group consisting of a radiographic guide, a dental impression, and a portion of the patient's actual anatomical situation.

14. A non-transitory computer-readable storage medium having recorded thereon computer-executable instructions for virtually planning a cranial drilled implant guided surgery of a patient, said computer-executable instructions, when running on one or more processors, performing a method comprising:
- virtually planning a position for an anchoring sleeve of a surgical template with one or more computer processors, based on a position of an artificial physical reference structure on said patient having a defined relation to a bone structure of said patient, wherein said artificial physical reference structure is a temporary anchoring implant, a pre-existing implant, or an anchoring pin or screw,
- generating a first data set based on said virtually planned position for said anchoring sleeve and based on input data, obtained from said artificial physical reference structure,
- generating a second data set based on input data obtained from a master structure for said surgical template, said master structure having a defined relation to said artificial physical reference structure, and
- generating a third data set for production of said surgical template based on the first data set and the second data set, wherein the relation of said artificial physical reference structure to said master structure is preserved.

15. The computer-readable medium of claim 14, wherein said third data set is configured for subsequent use in production of a real surgical template, said real surgical template being configured for use in said cranial drilled implant guided surgery.

16. The computer-readable medium of claim 14, wherein said third data set is configured for subsequent use in production of a real surgical template, said real surgical template being configured for use in controlling a device configured to facilitate said cranial drilled implant guided surgery.

17. A computer-implemented method of virtually planning a cranial guided surgery in a subject, said method comprising
- generating a first data set based on input data obtained of an artificial physical reference structure positioned on said subject having a defined fixed relation to a bone structure of said subject,
- generating a second data set based on input data of a master structure for a surgical template, said master structure having a defined relation to said artificial physical reference structure, and
- generating a third data set for production of said surgical template based on the first data set and the second data set, wherein the relation of said artificial physical reference structure to said master structure is preserved,
- wherein the artificial physical reference structure is a pre-existing implant, and wherein said surgical template of said third data set is lockable into a correct position by a template abutment interlocking to the pre-existing implant.

18. A computer-implemented method of virtually planning a cranial guided surgery in a subject, said method comprising
- virtually planning a position for an anchoring sleeve of a surgical template with one or more computer processors, based on a position of an artificial physical reference structure positioned on said subject having a defined fixed relation to a bone structure of said subject, wherein said artificial physical reference structure is an anchoring pin or anchor screw,
- generating a first data set based on said virtually planned position for said anchoring sleeve and based on input data obtained of said artificial physical reference structure,
- generating a second data set based on input data of a master structure for said surgical template, said master structure having a defined relation to said artificial physical reference structure, and
- generating a third data set for production of said surgical template based on the first data set and the second data set, wherein the relation of said artificial physical reference structure to said master structure is preserved.

* * * * *

UNITED STATES PATENT AND TRADEMARK OFFICE
CERTIFICATE OF CORRECTION

PATENT NO. : 8,805,658 B2  
APPLICATION NO. : 12/933140  
DATED : August 12, 2014  
INVENTOR(S) : Andreas Pettersson, Izidor Brajnovic and Henrik Petersson Page 1 of 1

It is certified that error appears in the above-identified patent and that said Letters Patent is hereby corrected as shown below:

On the Title Page
   In column 2 (page 1, item 56) line 14, References cited Under Other Publications, change "Maxilafacial" to --Maxillofacial--.

In the Specification
   In column 14 line 64, Change "and or" to --and/or--.

In the Claims
   In column 24 line 40, In Claim 12, change "processing processor" to --processors--.

Signed and Sealed this
Thirty-first Day of March, 2015

Michelle K. Lee
*Director of the United States Patent and Trademark Office*